United States Patent [19]

Shiraishi et al.

[11] Patent Number: 5,270,308
[45] Date of Patent: Dec. 14, 1993

[54] 1,3-BENZOXAZINE DERIVATIVES, THEIR PRODUCTION AND USE

[75] Inventors: Mitsuru Shiraishi, Amagasaki; Shohei Hashiguchi, Nagoya; Toshifumi Watanabe, Kawachinagano, all of Japan

[73] Assignee: Takeda Chemical Industries, Ltd., Osaka, Japan

[21] Appl. No.: 764,692

[22] Filed: Sep. 25, 1991

[30] Foreign Application Priority Data

| Sep. 25, 1990 | [JP] | Japan | 2-256478 |
| Dec. 28, 1990 | [JP] | Japan | 2-417050 |
| Mar. 15, 1991 | [JP] | Japan | 3-076742 |
| Aug. 14, 1991 | [JP] | Japan | 3-204235 |

[51] Int. Cl.$^5$ ............ A61K 31/535; C07D 265/12; C07D 265/16; C07D 498/04
[52] U.S. Cl. ............ 514/229.8; 514/230.5; 544/71; 544/89; 544/90; 544/95
[58] Field of Search ............ 540/454, 460, 488, 492, 540/544, 553; 544/54, 55, 69, 70, 73, 89, 90, 95, 71; 514/183, 211, 218, 226.8, 229.8, 230.5

[56] References Cited

U.S. PATENT DOCUMENTS

| 4,971,982 | 11/1990 | Attwood et al. | 514/337 |
| 5,036,068 | 7/1991 | Baumgarth et al. | 544/90 |

FOREIGN PATENT DOCUMENTS

| 076075 | 4/1983 | European Pat. Off. |
| 0339562 | 11/1989 | European Pat. Off. |
| 371312 | 6/1990 | European Pat. Off. |
| 0432893 | 6/1991 | European Pat. Off. |
| 2321496 | 11/1974 | Fed. Rep. of Germany |

OTHER PUBLICATIONS

Sankyo Co., Chemical Abstract vol. 98, No. 16704s (JP 57-130,979, 1982).
King et al., Chem. Abstract vol. 57, No. 11179g (1962).

Primary Examiner—Mukund J. Shah
Assistant Examiner—Philip Datlow
Attorney, Agent, or Firm—Wegner, Cantor, Mueller & Player

[57] ABSTRACT

A new compound of the formula:

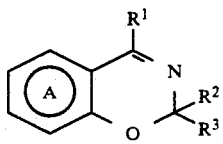

(I)

wherein

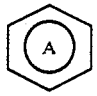

is an optionally substituted benzene ring; $R^1$ is a carbocyclic or heterocyclic group which is linked to the 4-position of the 1,3-benzoxazine ring through a carbon-carbon bond, a hydrocarbon residue, etc.; and $R^2$ and $R^3$ are independently a hydrogen atom or an optionally substituted $C_{1-6}$ alkyl group, etc., or a salt thereof is useful for treating and preventing heart, circulatory, respiratory and cerebral diseases.

12 Claims, No Drawings

1,3-BENZOXAZINE DERIVATIVES, THEIR PRODUCTION AND USE

FIELD OF THE INVENTION

The present invention relates to novel 1,3-benzoxazine derivatives and salts thereof which are useful as drugs. The novel 1,3-benzoxazine derivatives of the present invention have smooth muscle relaxation activities and are useful for treating and preventing heart and circulatory diseases such as congestive heart failure, angina pectoris, arrhythmia, hypertension and the like, urinary incontinence, respiratory diseases such as asthma and the like, cerebral diseases such as cerebrovascular contraction, cerebral hemorrhage, epilepsia and the like.

BACKGROUND OF THE INVENTION

As drugs having smooth muscle relaxation activities, drugs acting on a contraction system and those acting on a relaxation system are known. As the drugs acting on a contraction system, there are β-blockers, $\alpha_1$-blockers, calcium antagonists and the like. As the drugs acting on a relaxation system, there are nitro compounds, and the like.

A new type of drug called a potassium channel opener has recently been noted. The drug opens (activates) potassium channels to exhibit smooth muscle relaxation activities.

As an effect to be expected for a potassium channel opener, for example, when hypotensive activity is considered, the drug can exhibit vasodilation activity without any influence on calcium channels and any function based on calcium channels of other organs (e.g., heart) is not impaired. The potassium channel opener can therefore be a drug which has few side effects of inhibitory activity on heart function and has potent hypotensive activity.

For example, chroman-3-ol derivatives which have potassium channel opening (activating) activity and exhibit hypotensive activity on spontaneously hypertensive rats are disclosed in JP-A 58-67683, J. Med. Chem., 29, 2194–2201 (1986) and Br. J. Pharmac. 88, 103–111 (1986). Further, other compounds having potassium channel opening activities are also disclosed in JP-A 57-130979, EP-A 298452 and EP-A 371312.

OBJECTS OF THE INVENTION

The main object of the present invention is to provide novel 1,3-benzoxazine derivatives and salts thereof which have smooth muscle relaxation activities and are useful for the treatment and prevention of heart and circulatory diseases such as angina pectoris, arrhythmia, heart failure, hypertension, angiemphractic disease (Raynaud's disease) and the like, cerebral diseases such as cerebrovascular contraction, cerebral hemorrhage, epilepsia, and the like, asthma, urinary incontinence (irritant bladder disease), and the like as well as for the local treatment of alopecia.

This object as well as other objects and advantages of the present invention will become apparent to those skilled in the art from the following description.

SUMMARY OF THE INVENTION

According to the present invention, there is provided:

(1) A 1,3-benzoxazine derivative of the general formula (I):

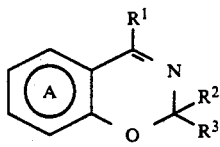

wherein

is an optionally substituted benzene ring; $R^1$ is a carbocyclic or heterocyclic group which is linked to the 4-position of the 1,3-benzoxazine ring through a carbon-carbon bond, a hydrocarbon residue or a group of the formula:

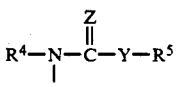

(wherein $R^4$ is a hydrogen atom, a $C_{1-4}$ alkyl group or a $C_{1-4}$ alkylcarbonyl group; Y is —S—, —O— or a group of the formula:

(wherein $R^6$ is a hydrogen atom, a $C_{1-4}$ alkyl or a $C_{1-11}$ acyl group); Z is =N—CN, =N—NO$_2$ or =CH—NO$_2$; and $R^5$ is a hydrogen atom or a $C_{1-8}$ alkyl group, or $R^4$ and $R^5$ are linked together to form a $C_{3-6}$ alkylene group or a $C_{3-6}$ alkylene carbonyl group, or $R^5$ and $R^6$ are linked together to form a $C_{4-5}$ alkylene group), the carbocyclic or heterocyclic group and the hydrocarbon residue may be optionally substituted; and $R^2$ and $R^3$ are independently a hydrogen atom or an optionally substituted $C_{1-6}$ alkyl group, or $R^2$ and $R^3$ are linked together to form an optionally substituted $C_{3-6}$ alkylene group; or a salt thereof.

(2) A process for producing the compound of the general formula (I) or a salt thereof which comprises reacting a compound of the general formula (II):

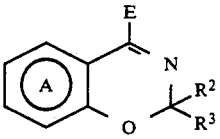

E is a halogen atom or an esterified hydroxyl group and the other symbols are as defined above, or a salt thereof with a compound of the general formula (IV):

R$^{1'}$-M     (IV)

wherein R$^{1'}$ is a carbocyclic or heterocyclic group which is linked to the group M through its carbon atom, a hydrocarbon residue or a group of the formula:

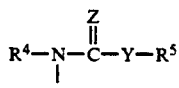

(wherein $R^4$ is a hydrogen atom, a $C_{1-4}$ alkyl group or a $C_{1-4}$ alkylcarbonyl group; Y is —S—, —O— or a group of the formula:

(wherein $R^6$ is a hydrogen atom, a $C_{1-4}$ alkyl or a $C_{1-11}$ acyl group); Z is =N—CN, =N—NO$_2$ or =CH—NO$_2$; $R^5$ a is hydrogen atom or a $C_{1-8}$ alkyl group, or $R^4$ and $R^5$ are linked together to form a $C_{3-6}$ alkylene group or a $C_{3-6}$ alkylene carbonyl group, or $R^5$ and $R^6$ are linked together to form a $C_{4-5}$ alkylene group), the carbocyclic or heterocyclic group and the hydrocarbon residue may be optionally substituted; and M is a leaving group.

(3) A process for producing the compound of the general formula (I) or a salt thereof which comprises reacting a compound of the general formula (VII):

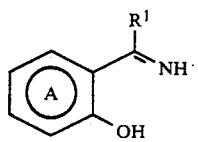 (VII)

wherein each symbols is as defined above, with a compound of the general formula (VIII) or (VIII'):

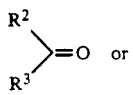 (VIII)

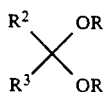 (VIII')

wherein R is methyl or ethyl group and the other symbols are as defined above, or a salt thereof.

(4) A process for producing the compound of the general formula (I) or a salt thereof which comprises reacting a compound of the general formula (IX):

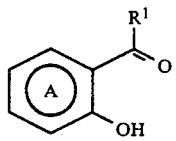 (IX)

wherein each symbol is as defined above or a salt thereof, with the compound of the general formula (VIII) or (VIII') and ammonia.

(5) A hypotensor which comprises the compound of the general formula (I) or a salt thereof.

DETAILED DISCLOSURE OF THE INVENTION

In the above formulas, the optionally substituted benzene ring represented by the formula:

includes an unsubstituted benzene ring and benzene ring substituted by 1 to 2 substituents. When the ring is substituted with 2 substituents, the substituents may be linked together to form a further ring.

Representative examples of the compound of the formula (I) include, for example, compounds of the formula (Ia):

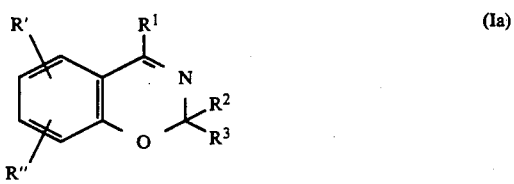 (Ia)

wherein $R^1$, $R^2$ and $R^3$ are as defined above; and R' and R" are independently a hydrogen atom, a hydroxyl group, a halogen atom, a nitro group, a cyano group, an optionally substituted $C_{1-6}$ alkyl group, an optionally substituted $C_{1-6}$ alkoxy group, an optionally substituted $C_{2-6}$ alkenyl group, an optionally substituted ethynyl group, an optionally substituted aryl group, an optionally substituted heteroaryl group, an optionally substituted amino group, an optionally substituted carbonyl group, an optionally substituted carboxyl group, an optionally substituted carbonyloxy group, an optionally substituted thiocarbonyl group, an optionally substituted thiocarbonyloxy group, an optionally substituted iminoalkyl group, an optionally substituted mercapto group, an optionally substituted sulfinyl group or an optionally substituted sulfonyl group, or R' and R" are linked together to form —CH=CH—CH=CH— (which is optionally substituted with 1 to 3 substituents selected from the group consisting of $C_{1-4}$ alkyl, $C_{1-4}$ alkoxy, nitro, halogen, $CF_3$, $C_{1-4}$ alkoxycarbonyl and cyano), =N—O—N=, —(CH$_2$)$_a$— (wherein a is 3 or 4), —(CH$_2$)$_b$—CO—, —(CH$_2$)$_b$—C(=NOH)— or —(CH$_2$)$_b$—C(=N—O— alkyl)- (wherein b is 2 or 3).

R' and R" of the 1,3-benzoxazine derivatives of the general formula (Ia) are preferably at 6- and 7-positions of the 1,3-benzoxazine nucleus. These groups may be, however, at 5- and 6-positions, 5- and 7-positions, 5- and 8-positions, 6- and 8-positions or 7- and 8-positions. When one of R' and R" is hydrogen and the other is a group other than hydrogen, the other group is preferably at the 6-position, but it may be at the 5-, 7- or 8-position. When both R' and R" are not hydrogen or linked together, they are preferably at the 6- and 7-positions, but may be at the 5- and 6-positions or 7- and 8-positions.

As the substituents in the optionally substituted alkyl, alkoxy, alkenyl, aryl and heteroaryl groups of of R' and R", there are one or more substituents selected from the group consisting of $C_{1-4}$ alkyl, $C_{1-4}$ alkoxy, aryl, arylalkyl, hydroxyl, nitro, halogen and cyano. The aryl group of these substituents may be optionally substituted with one or more groups selected from the group consisting of $C_{1-4}$ alkyl, $C_{1-4}$ alkoxy, hydroxyl, nitro, halogen, halo $C_{1-4}$ alkyl (e.g., $CF_3$, etc.), cyano, halo $C_{1-4}$ alkoxy (e.g., $CF_3O$, etc.), mercapto and halo $C_{1-4}$ alkylthio (e.g., CF$_3$S, etc.). As the substituents in the optionally substituted ethynyl group, there are trimethylsilyl group as well as the same substituents as those in the above alkyl, alkoxy, alkenyl, aryl and heteroaryl. As the substituents in the optionally substituted amino, there are $C_{1-4}$ alkyl, $C_{1-4}$ alkoxy, halo $C_{1-4}$ alkyl (e.g., CF$_3$, etc.), formyl, thioformyl, hydroxyl, carbamoyl, aryl, arylalkyl, $C_{1-4}$ alkylcarbonyl, arylcarbonyl, arylalkylcarbonyl, alkyloxycarbonyl, aryloxycarbonyl, arylalkyloxycarbonyl, heteroarylcarbonyl, $C_{1-4}$ alkylsulfinyl, $C_{1-4}$ alkoxysulfinyl, arylsulfinyl, $C_{1-4}$ alkylsulfonyl, $C_{1-4}$ alkoxysulfonyl and arylsulfonyl. The aryl in these substituent groups may also be optionally substituted with one or more substituents selected from the group consisting of $C_{1-4}$ alkyl, $C_{1-4}$ alkoxy, hydroxy, nitro, halogen, halo $C_{1-4}$ alkyl (e.g., CF$_3$, etc.), cyano, halo $C_{1-4}$ alkoxy (e.g., CF$_3$O, etc.), mercapto and halo $C_{1-4}$ alkylthio (e.g., CF$_3$S, etc.). As the substituents in the optionally substituted carbonyl and thiocarbonyl, there are $C_{1-4}$ alkyl, amino, $C_{1-4}$ alkylamino, $C_{1-4}$ alkyloxycarbonylamino (e.g., di-t-butyloxycarbonylamino, etc.) arylamino, arylalkylamino, heteroarylamino, heteroarylalkylamino, aryl, arylalkyl, heteroarylalkyl and heteroaryl. The nuclei of the aryl and heteroaryl may optionally be further substituted as described above. As the substituents in the optionally substituted carbonyloxy and thiocarbonyloxy, there are the same substituents as those in the above carbonyl and thiocarbonyl. As the substituents in the optionally substituted carboxyl, there are $C_{1-4}$ alkyl and arylalkyl and the nucleus of the aryl may optionally be substituted as described above. As the substituents in the optionally substituted iminoalkyl, there are hydroxy, amino, $C_{1-4}$ alkyl, $C_{1-4}$ alkoxy, aryl, arylalkyloxy and heteroarylalkyloxy and the nuclei of the aryl and heteroaryl may optionally be substituted as described above. As the substituents in the optionally substituted mercapto, there are $C_{1-4}$ alkyl, aryl, heteroaryl, arylalkyl and halo $C_{1-4}$ alkyl (e.g., CF$_3$, etc.). As the substituents in the optionally substituted sulfinyl and sulfonyl, there are $C_{1-4}$ alkyl, $C_{1-4}$ alkoxy, aryl, heteroaryl, arylalkyl and amino. The nuclei of these aryl and heteroaryl may be further substituted as described above.

R' and R" are preferably methyl, ethyl, acetyl, propionyl, benzoyl (optionally substituted with methyl, methoxy, halogen, nitro, CF$_3$ or cyano), methoxy, ethoxy, methoxycarbonyl, ethoxycarbonyl, acetoxy, propioxy, propoxycarbonyl, butyloxycarbonyl, isobutyloxycarbonyl, 1-hydroxyethyl, 1-hydroxybenzyl, methylsulfinyl, ethylsulfinyl, benzenesulfinyl (optionally substituted with methyl, methoxy, halogen, nitro, CF$_3$ or cyano), methylsulfonyl, ethylsulfonyl, benzenesulfonyl (optionally substituted with methyl, ethoxy, halogen, nitro, CF$_3$ or cyano), methoxysulfinyl, ethoxysulfinyl, methoxysulfonyl, ethoxysulfonyl, acetamido, propionamido, benzamido (optionally substituted with methyl, methoxy, halogen, nitro, CF$_3$ or cyano), methoxycarbonylamido, ethoxycarbonylamido, thioacetyl, thiopropionyl, thiobenzoyl (optionally substituted with methyl, methoxy, halogen, nitro, CF$_3$ or cyano), methoxythiocarbonyl, ethoxythiocarbonyl, thionoacetoxy, thionopropionoxy, 1-mercaptoethyl, 1-mercaptobenzyl, methylsulfinylamino, ethylsulfinylamino, benzenesulfinylamino (optionally substituted with methyl, methoxy, halogen, nitro, CF$_3$ or cyano), methylsulfonylamino, ethylsulfonylamino, benzenesulfonylamino (optionally substituted with methyl, methoxy, halogen, nitro, CF$_3$ or cyano), methoxylsulfinylamino, ethoxylsulfinylamino, methoxysulfonylamino, ethoxysulfonylamino, 1-propenyl, styryl (optionally substituted with methyl, methoxy, halogen, nitro, CF$_3$ or cyano), methoxyiminomethyl, ethoxyiminomethyl, 1-(hydroxyimino)ethyl, 1-(hydroxyimino)propyl, 1-hydrazinoethyl, 1-hydrazinopropyl, 1-propynyl, CF$_3$, CF$_3$CF$_2$, CF$_3$O, HCF$_2$O, CF$_2$=CF, nitro, cyano, halogen, amino, formyl, formamido, hydroxyiminomethyl, CO$_2$H, CONH$_2$, SH, CF$_3$S, thioformamido, CSNH$_2$, SO$_2$NH$_2$, 2-oxopropyl, 2-oxobutyl, 3-oxobutyl, 3-oxopentyl, nitromethyl, 1-nitroethyl, 2-nitroethyl, vinyl, nitrovinyl, cyanovinyl, trifluorovinyl, ethynyl or (CH$_3$)$_3$SiC≡C.

R' and R" are more preferably methyl, ethyl, acetyl, benzoyl (optionally substituted with methyl, methoxy, halogen, nitro, CF$_3$ or cyano), methoxycarbonyl, methylsulfonyl, benzenesulfonyl (optionally substituted with methyl, ethoxy, halogen, nitro, CF$_3$ or cyano), CF$_3$, CF$_3$CF$_2$, CF$_3$O, CF$_2$=CF, nitro, cyano, halogen, cyano, amino, formyl, CO$_2$H, CONH$_2$, nitromethyl or ethynyl.

The heteroaryl group in R' and R" is five or six membered monocyclic or nine or ten membered bicyclic heteroaryl, preferably five or six membered monocyclic heteroaryl. The five or six membered monocyclic or nine or ten membered bicyclic heteroaryl contains one, two or three heteroatoms selected from the group consisting of oxygen, nitrogen and sulfur and, when it contains two or more heteroatoms, they may be the same or different. Examples of the five or six membered monocyclic heteroaryl containing one, two or three heteroatoms selected from the group consisting of oxygen, nitrogen and sulfur includes furyl, thienyl, pyrrolyl, oxazolyl, thiazolyl, imidazolyl, oxadiazolyl, thiadiazolyl, pyridyl, pyridazinyl, pyrimidinyl, pyrazinyl and triazinyl. Examples of the nine or ten membered bicyclic heteroaryl group containing one, two or three heteroatoms selected from the group consisting of oxygen, nitrogen and sulfur include benzofuranyl, benzothienyl, indolyl, indazolyl, quinolyl, isoquinolyl and quinazolinyl.

Preferred examples of the substituent of the optionally substituted heteroaryl is methyl, methoxy, halogen, CF$_3$, nitro or cyano.

When R' and R" are linked together, they preferably form —CH=CH—CH=CH— (optionally substituted with methyl, methoxy, halogen, nitro, CF$_3$ or cyano), =N—O—N=, —(CH$_2$)$_3$—, —(CH$_2$)$_4$—, —(CH$_2$)$_2$CO—, —(CH$_2$)$_3$CO—, —(CH$_2$)$_2$C(=NOH)—, —(CH$_2$)$_2$C(=NOCH$_3$)—, —(CH$_2$)$_3$C(=NOH)— or (CH$_2$)$_3$C(=NOCH$_3$)—.

As the optionally substituted carbocyclic or heterocyclic group of R$^1$ which is linked to the 4-position of the 1,3-benzoxazine ring, there are phenyl, 2-pyridyl, 3-pyridyl, 4-pyridyl, 1-$C_{1-4}$ alkylpyridium-2-yl, 1-$C_{1-4}$ alkylpyridium-3-yl, 1-$C_{1-4}$ alkylpyridium-4-yl, pyridin-N-oxide-2-yl, pyridin-N-oxide-3-yl, pyridin-N-oxide-4-yl, 3 or 4-pyridazinyl, pyridazin-N-oxide-3 or 4-yl, 4 or 5-pyrimidinyl, pyrimidin-N-oxide-4 or 5-yl, 2-pyrazinyl, pyrazin-N-oxide-2 or 3-yl, 2-quinolinyl, 3-quinolinyl, 4-quinolinyl, quinolin-N-oxide-2-yl, quinolin-N-oxide-3-yl, quinolin-N-oxide-4-yl, isoquinolin-1,3 or 4-yl, isoquinolin-N-oxide-1,3 or 4-yl, 2- or 3-indolyl, 2- or 3-pyrrolyl, groups of the formulas:

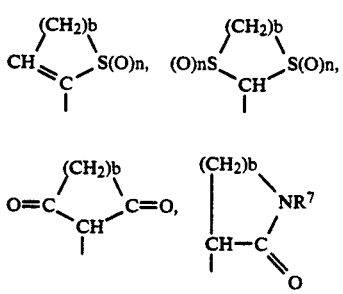

(wherein b is as defined above; n is 0, 1 or 2; and $R^7$ is hydrogen, $C_{1-6}$ alkyl, nitroxy $C_{1-4}$ alkyl or aryl), 2,2-dimethyl-1,3-dioxan-4,6-dione-5-yl and the like. As the optionally substituted hydrocarbon residue, there are $\{R^7S(O)n\}_2CH—$, $(R^7CO)_2—CH—$ (wherein each symbol is as defined above and each of the groups is unsubstituted or optionally substituted with one to three substituents selected from the group consisting of halogen, $C_{1-4}$ alkyl, $C_{1-4}$ alkoxy, nitro, hydroxy $C_{1-4}$ alkyloxy, hydroxy $C_{1-4}$ alkylaminocarbonyl, trimethylsilyl, trimethylsilyl $C_{1-4}$ alkyloxymethyloxy, nitroxy $C_{1-4}$ alkyloxy, nitroxy $C_{1-4}$ alkylaminocarbonyl, $CF_3$, $CF_3O$, $C_{1-4}$ alkylsulfonyl, arylsulfonyl, $C_{1-4}$ alkylcarbonyl, arylcarbonylcyano, $CO_2H$, $C_{1-4}$ alkoxycarbonyl, $NH_2$, $C_{1-8}$ alkanoylamino, $C_{7-11}$ aroylamino, 3-$C_{1-8}$ alkyl-2-cyano and nitroguanidino) and the like.

$R^1$ is preferably phenyl, tolyl, methoxyphenyl, dimethoxyphenyl, trimethoxyphenyl, hydroxyphenyl, halogenophenyl, nitrophenyl, $CF_3$-phenyl, $CF_3O$-phenyl, cyanophenyl, carboxyphenyl, methoxycarbonylphenyl, ethoxycarbonylphenyl, aminophenyl, acetamidophenyl, methylthiophenyl, methylsulfinylphenyl, methanesulfonylphenyl, benzenesulfonylphenyl, toluenesulfonylphenyl, hydroxyethoxyphenyl, hydroxypropoxyphenyl, hydroxyethylaminocarbonylphenyl, nitroxyethoxyphenyl, nitroxypropoxyphenyl, nitroxyethylaminocarbonylphenyl, [3-(t-butyl)-2-cyano (or nitro) guanidino]phenyl, [3-(1,2,2-trimethylpropyl)-2-cyano (or nitro) guanidino]phenyl, 2-pyridyl, 3-pyridyl, 4-pyridyl, 1-methylpyridinium-2-yl, 1-methylpyridinium-3-yl, 1-methylpyridinium-4-yl, pyridin-N-oxide-2-yl, pyridin-N-oxide-3-yl, pyridine-N-oxide-4-yl, (di)methylpyridin 2,3 or 4-yl, (di)methylpyridin-N-oxide-2,3 or 4-yl, hydroxypyridin-2,3 or 4-yl, hydroxypyridin-N-oxide-2,3 or 4-yl, methoxypyridin-2,3 or 4-yl, methoxypyridin-N-oxide-2,3 or 4-yl, ethoxypyridin-2,3 or 4-yl, ethoxypyridin-N-oxide-2,3 or 4-yl, halogenopyridin-2,3 or 4-yl, halogenopyridin-N-oxide-2,3 or 4-yl, nitropyridin-2,3 or 4-yl, nitropyridin-N-oxide-2,3 or 4yl, aminopyridin-2,3 or 4-yl, aminopyridin-N-oxide-2,3 or 4-yl, trifluoromethylpyridin-2,3 or 4-yl, trifluoromethylpyridin-N-oxide-2,3 or 4-yl, nitroxyethoxypyridin-2,3 or 4-yl, nitroxyethoxypyridin-N-oxide-2,3 or 4-yl, carboxypyridin-2,3 or 4-yl, carboxypyridin-N-oxide-2,3 or 4-yl, methoxycarbonylpyridin-2,3 or 4-yl, methoxycarbonylpyridin-N-oxide-2,3 or 4-yl, ethoxycarbonylpyridin-2,3 or 4-yl, ethoxycarbonylpyridin-N-oxide-2,3 or4-yl, carbamoylpyridin-2,3 or 4-yl, carbamoylpyridin-N-oxide-2,3 or 4-yl, cyanopyridin-2,3 or 4-yl, cyanopyridin-N-oxide-2,3 or 4-yl, nitroxyethylaminocarbonylpyridin-2,3 or 4-yl, nitroxyethylaminocarbonylpyridin-N-oxide-2,3 or 4-yl, [3-methyl-2-cyano (or nitro) guanidino]pyridin-2,3 or 4-yl, [3-methyl-2-cyano (or nitro) guanidino]pyridine-N-oxide-2,3 or 4-yl, [3-(t-butyl)-2-cyano (or nitro) guanidino]pyridin-2,3 or 4-yl, [3-(t-butyl)-2-cyano (or nitro) guanidino]pyridine-N-oxide-2,3 or 4-yl, [3-(1,2,2-trimethylpropyl)-2-cyano (or nitro) guanidino]pyridin-2,3 or 4-yl, [3-(1,2,2-trimethylpropyl)-2-cyano (or nitro) guanidino]pyridin-N-oxide-2,3 or 4-yl, acetamidopyridin-2,3 or 4-yl, acetamidopyridin-N-oxide-2,3 or 4-yl, methanesulfonylpyridin-2,3 or 4-yl, methanesulfonylpyridin-N-oxide-2,3 or 4-yl, toluenesulfonylpyridin-2,3 or 4-yl, toluenesulfonylpyridin-N-oxide-2,3 or 4 yl, halogeno-nitropyridin-2,3 or 4-yl, halogeno-nitropyridin-N-oxide-2,3 or 4-yl, methyl-nitropyridin-2,3 or 4-yl, methyl-nitropyridin-N-oxide-2,3 or 4-yl, amino-nitropyridin-2,3 or 4-yl, amino-nitropyridin-N-oxide-2,3 or 4-yl, trifluoromethyl-halogenopyridin-2,3 or 4-yl, trifluoromethyl-halogenopyridin-N-oxide-2,3 or 4-yl, cyano-nitropyridin-2,3 or 4-yl, cyano-nitropyridin-N-oxide-2,3 or 4-yl, methyl-nitroxyethylaminocarbonylpyridin-2,3 or 4-yl, methyl-nitroxyethylaminocarbonylpyridin-N-oxide-2,3 or 4-yl, 3-pyridazinyl, 4-pyridazinyl, 6-methylpyridazin-3-yl, 6-methoxypyridazin-3-yl, 6-chloropyridazin-3-yl, pyridazine-N-oxide-3 or 4-yl, 6-methylpyridazin-N-oxide-3-yl, 6-methoxypyridazine-N-oxide-3-yl, 6-chloropyridazin-N-oxide-3-yl, 4-pyrimidinyl, 5-pyrimidinyl, 6-methylpyrimidin-4-yl, pyrimidine-N-oxide-4 or -5-yl, 6-methylpyrimidin-N-oxide-4-yl, 2-pyrazinyl, pyrazine-N-oxide-2 or 3-yl, 2-quinolinyl, 3-quinolinyl, 4-quinolinyl, nitroquinolin-2-yl, chloroquinolin-2-yl, methylquinolin-2-yl, methoxyquinolin-2-yl, quinolin-N-oxide-2,3 or 4-yl, nitroquinolin-N-oxide-2-yl, chloroquinolin-N-oxide-2-yl, methylquinolin-N-oxide-2-yl, methoxyquinolin-N-oxide-2-yl, isoquinolin-1,3 or 4-yl, isoquinolin-N-oxide-1,3 or 4-yl, 2- or 3-indolyl, N-acetylindol-2 or 3-yl, N-benzylindol-2 or 3-yl, N-methylsulfonylindol-2 or 3-yl, N-benzenesulfonylindol-2 or 3-yl, N-tosylindol-2 or 3-yl, 2 or 3-pyrrolyl, N-acetylpyrrol-2 or 3-yl, N-benzylpyrrol-2 or 3-yl, N-methylsulfonylpyrrol-2 or 3-yl, N-benzenesulfonylpyrrol-2 or 3-yl, N-tosylpyrrol-2 or 3-yl, groups of the formulas:

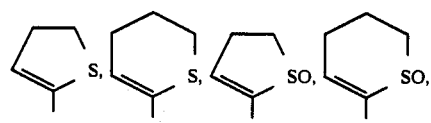

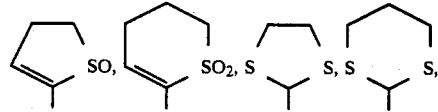

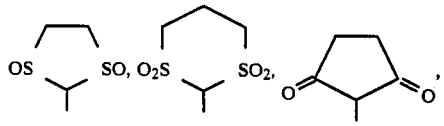

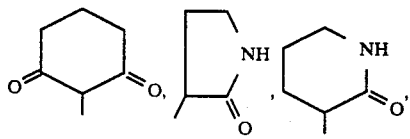

-continued

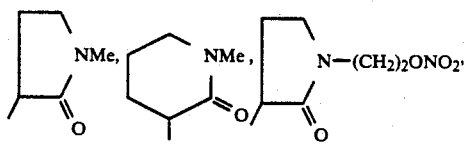

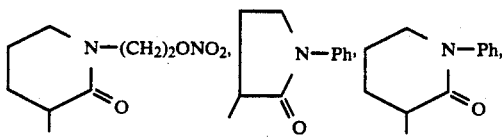

2,2-dimethyl-1,3-dioxan-4,6-dione-5-yl, (CH₃S)₂CH—, (PhS)₂CH—, (CH₃SO)₂CH—, (PhSO)₂CH—, (CH₃SO₂)₂CH—, (PhSO₂)₂CH—, Ac₂CH—, or (PhCO)₂CH—.

Particularly preferred R¹ is 2-pyridyl optionally substituted with hydroxy, lower alkoxy, lower alkyl or halogen, pyridine-N-oxide-2-yl optionally substituted with hydroxy, lower alkoxy, lower alkyl or halogen, 2-quinolyl, quinoline-N-oxide-2-yl, 1-methyl-2-oxo-3-pyrrolidinyl.

It is also preferred that R¹ is 3-methyl-2-cyano or nitro-guanidino, 3,3-dimethyl-2-cyano or nitro-guanidino, 3-(t-butyl)-2-cyano or nitro-guanidino, 3-(1,2,2-trimethylpropyl)-2-cyano or nitro-guanidino, 3-isopropyl-2-cyano or nitro-guanidino, 3-cyclopropyl-2-cyano or nitro-guanidino, 3,3-tetramethylene-2-cyano or nitro-guanidino, 3,3-pentamethylene-2-cyano or nitro-guanidino, (1-methylamino-2-nitroethenyl)amino, (1-isopropylamino-2-nitroethenyl)amino, 2-methyl-3-cyano or nitro-1-isothioureido, (1-methylthio-2-nitroethenyl)amino, 2-methyl-3-cyano or nitro-1-isoureido, 2-ethyl-3-cyano or nitro-1-isoureido, (1-methoxy-2-nitroethenyl)amino, (1-ethoxy-2-nitroethenyl)amino, 2-cyanoimino-imidazolidin-1-yl, 2-nitroimino-imidazolidin-1-yl, 2-cyanoimino or nitroimino-hexahydropyrimidin-1-yl, 2-nitroethenylimidazolidin-1-yl, 2-nitroethenyl-hexahydropyrimidin-1-yl, 2-cyanoimino or nitroimino-thiazolidin-3-yl, 2-nitroethenyl-thiazolidin-3-yl, 2-cyanoimino or nitroimino-oxazolidin-3-yl, 2-nitroethenyl-oxazolidin-3-yl, or 2-cyano or nitro-creatinin-3-yl.

Preferably, R² and R³ are independently methyl, ethyl or propyl.

When R² and R³ are linked together, they preferably form cyclopropyl, cyclopentyl or cyclohexyl.

The aryl in the above groups is preferably $C_{6-14}$ aryl such as phenyl, naphthyl, anthryl or the like.

The preferred examples of the novel 1,3-benzoxazine derivatives of the general fomula (I) of the present invention includes:

2,2-dimethyl-4-(2-pyridyl)-2H-1,3-benzoxazine,
2-(6-bromo-2,2-dimethyl-2H-1,3-benzoxazin-4-yl)pyridine N-oxide,
2-(6-cyano-2,2-dimethyl-2H-1,3-benzoxazin-4-yl)pyridine N-oxide,
2-(2,2-dimethyl-6-nitro-2H-1,3-benzoxazin-4-yl)pyridine N-oxide,
2-(6-acetyl-2,2-dimethyl-2H-1,3-benzoxazin-4-yl)pyridine N-oxide,
2-(6-cyano-2,2-dimethyl-7-nitro-2H-1,3-benzoxazin-4-yl)pyridine N-oxide,
2-(6-methoxycarbonyl-2,2-dimethyl-2H-1,3-benzoxazin-4-yl)pyridine N-oxide,
2-(6-ethynyl-2,2-dimethyl-2H-1,3-benzoxazin-4-yl)pyridine N-oxide,
2-(6-chloro-2,2-dimethyl-2H-1,3-benzoxazin-4-yl)pyridine N-oxide,
2-(6-bromo-2,2,7-trimethyl-2H-1,3-benzoxazin-4-yl)pyridine N-oxide,
2-(2,2,7-trimethyl-6-nitro-2H-1,3-benzoxazin-4-yl)pyridine N-oxide,
2-(6-cyano-2,2,7-trimethyl-2H-1,3-benzoxazin-4-yl)pyridine N-oxide,
2-(6-bromo-7-methoxy-2,2-dimethyl-2H-1,3-benzoxazin-4-yl)pypyridine N-oxide,
2-(7-methoxy-2,2-dimethyl-6-nitro-2H-1,3-benzoxazin-4-yl)pyridine N-oxide,
2-(6-cyano-7-methoxy-2,2-dimethyl-2H-1,3-benzoxazin-4-yl)pyridine N-oxide,
2-(6-bromo-7-fluoro-2,2-dimethyl-2H-1,3-benzoxazin-4-yl)pyridine N-oxide,
2-(6-cyano-7-fluoro-2,2-dimethyl-2H-1,3-benzoxazin-4-yl)pyridine N-oxide,
2-(7-fluoro-2,2-dimethyl-6-nitro-2H-1,3-benzoxazin-4-yl)pyridine N-oxide,
2-(6-trifluoromethyl-2,2-dimethyl-2H-1,3-benzoxazin-4-yl)pyridine N-oxide,
2-(6-trifluoromethoxy-2,2-dimethyl-2H-1,3-benzoxazin-4-yl)pyridine N-oxide,
2-(6-pentafluoroethyl-2,2-dimethyl-2H-1,3-benzoxazin-4-yl)pyridine N-oxide,
2-(6-trifluorovinyl-2,2-dimethyl-2H-1,3-benzoxazin-4-yl)pyridine N-oxide,
2-(6,7-dichloro-2,2-dimethyl-2H-1,3-benzoxazin-4-yl)pyridine N-oxide,
2-(6-bromo-7-chloro-2,2-dimethyl-2H-1,3-benzoxazin-4-yl)pyridine N-oxide,
2-(7-chloro-6-cyano-2,2-dimethyl-2H-1,3-benzoxazin-4-yl)pyridine N-oxide,
2-(6,7-dibromo-2,2-dimethyl-2H-1,3-benzoxazin-4-yl)pyridine N-oxide,
2-(2,2-dimethyl-2H-naphtho[2,3-e][1,3]oxazin-4-yl)pyridine N-oxide,
2-(6-cyano-2,2-dimethyl-2H-1,3-benzoxazin-4-yl)-3-ethoxypyridine N-oxide,
6-cyano-2,2-dimethyl-4-(1-methyl-2-oxo-3-pyrrolidinyl)-2H-1,3-benzoxazine,
2-(6-bromo-2,2-dimethyl-2H-1,3-benzoxazin-4-yl)quinoline N-oxide,
2-(6-cyano-2,2-dimethyl-2H-1,3-benzoxazin-4-yl)-3-methoxypyridine N-oxide,
2-(6-cyano-2,2-dimethyl-2H-1,3-benzoxazin-4-yl)-3-hydroxypyridine N-oxide,
2-(6-cyano-2,2-dimethyl-2H-1,3-benzoxazin-4-yl)-3-methylpyridine N-oxide,
3-chloro-2-(6-cyano-2,2-dimethyl-2H-1,3-benzoxazin-4-yl)pyridine N-oxide,
2-(6-bromo-2,2-dimethyl-2H-1,3-benzoxazin-4-yl)-3-methoxypyridine N-oxide,
2-(6-bromo-2,2-dimethyl-2H-1,3-benzoxazin-4-yl)-3-ethoxypyridine N-oxide,
2-(6-bromo-2,2-dimethyl-2H-1,3-benzoxaxin-4-yl)-3-methylpyridine N-oxide,
2-(6-bromo-2,2-dimethyl-2H-1,3-benzoxazin-4-yl)-3-chloropyridine N-oxide,
2-(6-bromo-7-chloro-2,2-dimethyl-2H-1,3-benzoxazin-4-yl)-3-methoxypyridine N-oxide,
2-(6-bromo-7-chloro-2,2-dimethyl-2H-1,3-benzoxazin-4-yl)-3-ethoxypyridine N-oxide,
2-(6-bromo-7-chloro-2,2-dimethyl-2H-1,3-benzoxazin-4-yl)-3-methylpyridine N-oxide, 2-(6-bromo-7-chloro-2,2-dimethyl-2H-1,3-benzoxazin-4-yl)-3-chloropyridine N-oxide,
2-(6-trifluoromethyl-2,2-dimethyl-2H-1,3-benzoxazin-4-yl)-3-methoxypyridine N-oxide,
3-ethoxy-2-(6-trifluoromethyl-2,2-dimethyl-2H-1,3-benzoxazin-4-yl)pyridine N-oxide,
2-(6-trifluoromethyl-2,2-dimethyl-2H-1,3-benzoxazin-4-yl)-3-methylpyridine N-oxide, and
3-chloro-2-(6-trifluoromethyl-2,2-dimethyl-2H-1,3-benzoxazin-4-yl)pyridine N-oxide.

The novel 1,3-benzoxazine derivatives of the general formula (I) of the present invention can be produced, for example, by reacting a compound of the general formula (II)

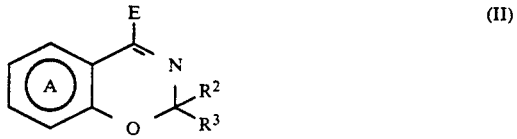

wherein

$R^2$ and $R^3$ are as defined above; and E is a halogen atom or an esterified hydroxyl group with an organic metal compound of the general formula (IV)

wherein $R^{1'}$ is as defined above; and M is a leaving group. The compound (IV) is easily produced by converting a compound of the general formula (III):

wherein $R^{1'}$ is a carbocyclic or heterocyclic group which is linked to another group through its carbon atom, a hydrocarbon residue or a group of the formula

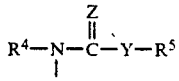

(wherein $R^4$ is a hydrogen atom, a $C_{1-4}$ alkyl group or a $C_{1-4}$ alkylcarbonyl group; Y is —S—, —O— or a group of the formula:

(wherein $R^6$ is a hydrogen atom, a $C_{1-4}$ alkyl group or a $C_{1-11}$ acyl group); Z is =N—CN, =N—NO$_2$ or =CH—NO$_2$; $R^5$ is a hydrogen atom or a $C_{1-8}$ alkyl group, or $R^4$ and $R^5$ are linked together to form a $C_{3-6}$ alkylene group or a $C_{3-6}$ alkylene carbonyl group, or $R^5$ and $R^6$ are linked together to form a $C_{4-5}$ alkylene group; the carbocyclic or heterocyclic group and the hydrocarbon residue may be optionally substituted; and W is a hydrogen atom or a halogen atom (Cl, Br, I) into the above compound (IV). If necessary, this converting reaction can be promoted smoothly by adding tetrakis(triphenylphosphine) palladium (O), tetrakis(triphenylphosphine)nickel (O) or the like as a catalyst.

The halogen atom represented by E in the general formula (II) is preferably chloro, bromo or iodo. The esterified hydroxyl group is preferably a hydroxyl group esterified with a reactive group such as trifluoromethansulfonyl, methansulfonyl, p-toluenesulfonyl or the like.

As the carbocyclic or heterocyclic group or hydrocarbon residue represented by $R^{1'}$ in the general formulas (III) and (IV) which is linked to the group M through its carbon atom, there are the groups similar to the carbocyclic or heterocyclic group or hydrocarbon residue represented by the above $R^1$ which is linked to 4-position of the 1,3-benzoxazine ring through carbon-carbon bond.

The leaving group represented by M in the general formula (IV) is preferably Li, Na, K, Ca($\frac{1}{2}$), MgCl, MgBr, MgI, ZnCl, SnCl, Sn(n-Bu)$_3$, CrCl$_2$, CuCl, CuBr, NiCl, PdCl or the like.

For example, this condensation reaction can be carried out at a temperature of about $-50°$ C. to $50°$ C. in an inert solvent such as tetrahydrofuran, diethyl ether, dimethoxyethane, hexane, toluene, benzene, methylene chloride, chloroform, 1,2-dichloroethane, DMF, DMSO or the like, or a mixture thereof. It is desired to appropriately change a solvent to be used according to a particular kind of the metal reagent because this reaction depends on ease of formation, stability, solubility in the solvent of the organic metal compound (IV) and the like. For example, in the case of an organic lithium compound and a Grignard reagent, tetrahydrofuran or diethyl ether is used and, in the case of an organic chrome reagent, DMF is used. This reaction is preferably carried out under an atmosphere of an inert gas such as nitrogen, argon or the like.

The organic metal compound (IV) can be obtained from the compound of the formula (III) according to a per se known method. For example, the reaction is carried out in an inert solvent as described above at a temperature of about $-78°$ C. to $70°$ C., preferably, under an atmosphere of an inert gas. In general, the compound of the formula (IV) is produced in the reaction system and then it is reacted without isolation with the compound of the formula (II) to obtain the compound of the formula (I).

The compound of formula (II) used as the starting material can be prepared according to a per se known method or the procedure described in the Reference Examples hereinafter.

Further, one or more groups of R', R" and/or $R^1$ in the compound of the formula (I) can be converted into different groups of R', R" and/or $R^1$. For example, a hydrogen atom can be substituted with a halogen atom by halogenation or a nitro group by nitration. Reduction of the nitro group can lead it to an amino group. Acylation or sulfonation of the amino group can lead it to an acylamino or sulfonylamino group. A cyano group can be converted into carbamoyl group by treatment with aqueous sodium hydroxide solution/30% hydrogen peroxide solution, and to thiocarbamoyl group by using hydrogen sulfide in pyridine/triethylamine. A cyano group can also be converted into carboxy group, for example, by heating in a sodium hydroxide solution to hydrolyze the cyano group. A cyano group can also be converted into a formyl group by using Raney nickel in water/acetic acid/pyridine in the presence of sodium phosphate. The formyl group can be converted into vinyl group by Wittig reaction, and to hydroxyiminomethyl group by the reaction with hydroxyamine, and the like. A hydroxyl group can be converted into an alkoxy group by alkylation, and to an acyloxy group by acylation. A hydroxyalkyl group can be converted to a nitroxyalkyl group by the treatment with sulfuric acid/nitric acid.

When $R^1$ is, for example, a pyridyl group, quinolyl group, isoquinolyl group or the like, such a group can be converted into a pyridine-N-oxide, quinoline-N-oxide, isoquinoline-N-oxide or the like, respectively, by oxidation with m-chloroperbenzoic acid, perbenzoic acid, p-nitroperbenzoic acid, pentafluoroperbenzoic acid, monoperphthalic acid, magnesium monoperoxyphthalate, peracetic acid, hydrogen peroxide or the like.

Preferably, the reaction condition of this reaction is appropriately changed depending upon a particular oxidant used. For example, when m-chloroperbenzoic acid is used, the reaction is carried out in an inert solvent such as dichloromethane, chloroform, 1,2-dichloroethane, diethyl ether, acetone, ethyl acetate and the like or a mixed solvent thereof at a temperature of $-25°$ C. to room temperature.

Alternatively, the compound of the general formula (I) can also be produced by a reaction as shown in the reaction scheme (I).

wherein

is as defined above; and M' is a leaving group and R''' is a protecting group of the hydroxy group, with a compound of the general formula (VI)

$$R^{1''}-CN \text{ (or } R^{1'''}-M') \quad \text{(VI)}$$

wherein $R^{1''}$ is a carbocyclic or heterocyclic group which is linked to the group CN through its carbon atom, a hydrocarbon residue or a group of the formula:

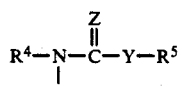

wherein each symbol is are as defined above, the carbocyclic or heterocyclic group and the hydrocarbon residue may be optionally substituted; $R^{1'''}$ is a carbocyclic or heterocyclic group which is linked to the group M' through its carbon atom, a hydrocarbon residue or a group of the formula:

Reaction scheme (I)

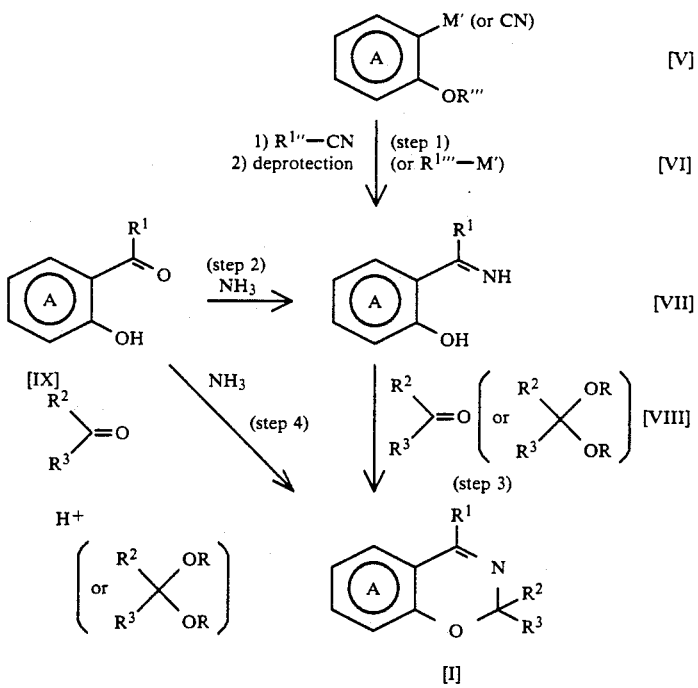

Namely, the desired compound can be produced by reacting the compound of the general formula (VI):

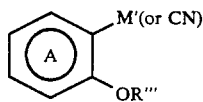

(V)

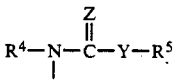

wherein each symbols are as defined above, the carbocyclic or heterocyclic group and the hydrocarbon residue may be optionally substituted; and M' is a leaving group, removing the protecting group according to a per se known method to obtain an imino compound of the general formula (VII):

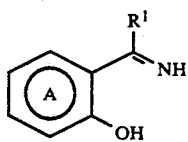 (VII)

wherein

and $R^1$ are as defined above and then reacting the imino compound (VII) with a compound of the general formula (VIII)a:

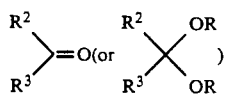 (VIII)

wherein $R^2$ and $R^3$ are as defined above; and R is methyl or ethyl group, in the presence of an acid catalyst to obtain the desired compound.

The imino compound of the general formula (VII) can be prepared by treating a compound of the general formula (IX):

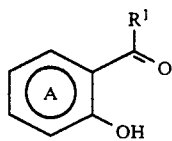 (IX)

wherein

and $R^1$ are as defined above, with ammonia.

Further, the compound of the general formula (I) can also be produced by reacting the compound of the general formula (IX) with the compound of the general formula (VIII) and ammonia at once in the presence of an acid catalyst The leaving group represented by M' in the general formulas (V) and (VI) is preferably Li, Na, K, Ca($\frac{1}{2}$), MgCl, MgBr, MgI, ZnCl, SnCl, CrCl$_2$ or the like.

The protecting group of the hydroxyl group represented by R''' in the general formula (V) is preferably a known protecting group for a phenolic hydroxyl group such as methoxydimethylmethyl group, trimethylsilyl group, t-butyldimethylsilyl group and the like.

Each step is illustrated in detail below.

Step 1:

The condensation reaction is carried out in an inert solvent such as tetrahydrofuran, diethyl ether, dimethoxyethane, hexane, toluene, benzene, methylene chloride, DMF or the like or a mixed solvent thereof at a temperature of about $-70°$ C. to $70°$ C. Preferably, this reaction is carried out under an atmosphere of an inert gas such as nitrogen, argon or the like.

The deprotection reaction is carried out by a per se known acid hydrolysis or a reaction with a fluoride salt such as tetrabutylammonium fluoride, potassium fluoride or the like.

The organic metal compound (V):

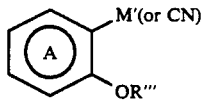 (V)

(or (VI) $R^1$-M') can be obtained by a per se known method according to the same manner as that described with respect to the above organic metal compound (IV) from the compound of the general formula (X):

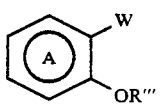 (X)

wherein

W and R''' are as defined above (or the compound of the general formula (III)).

Step 2:

The reaction of the hydroxyketone compound (IX) with ammonia is carried out in an inert solvent such as ethanol, benzene, toluene, chloroform, dichloromethane, 1,2-dichloroethane, tetrahydrofuran, diethyl ether or the like or a mixed solvent thereof at a temperature of about $0°$ C. to $100°$ C. Normally, this reaction is carried out in a sealed tube in a solvent containing a 1 to 10-fold molar amount of ammonia based on the hydroxyketone compound (IX) in the presence of a dehydrating agent such as molecular sieves, anhydrous calcium sulfate, anhydrous magnesium sulfate or the like.

The imino compound (VII) obtained in the steps 1 and 2 can be used in the next reaction without purification and isolation thereof.

Step 3:

The ring closure reaction between the imino compound (VII) and the compound (VIII) is carried out in the absence of any solvent or in an inert solvent such as benzene, toluene, chloroform, dichloromethane, 1,2-dichloroethane, diethyl ether or the like or a mixed solvent thereof in the presence of an acid catalyst and a dehydrating agent at a temperature of room temperature to $100°$ C.

Examples of the acid catalyst to be used include hydrochloric acid, p-toluenesulfonic acid, benzenesulfonic acid, camphorsulfonic acid, ammonium chloride, ammonium acetate and the like. The amount of the acid catalyst to be used can be appropriately changed depending upon the acidity of the catalyst and, preferably, within the range of about 1/100 to 10-fold molar amount based on the imino compound (VII).

Examples of the dehydrating agent to be used include molecular sieves, anhydrous calcium sulfate, anhydrous magnesium sulfate and the like.

Step 4:

The one-pot reaction of the hydroxyketone (IX) and ammonia with the compound (VIII) is carried out in the absence of any solvent or in an inert solvent such as benzene, toluene, chloroform, dichloromethane, 1,2-dichloroethane, diethyl ether or the like or a mixed solvent thereof in the presence of an acid catalyst and a dehydrating agent at a temperature of 0° C. to 100° C. Normally, this reaction is carried out in a sealed tube in a solvent containing an about 1 to 10-fold molar amount of ammonia based on the hydroxyketone compound (IX). As the acid catalyst, the catalysts as described in the step 3 can be used. The amount of the acid catalyst to be used is preferably in the range of an about 1/20 to 10-fold molar amount based on the hydroxyketone compound (IX). As the dehydrating agent, the dehydrating agents as described in the step 3 can be used.

The starting material in the reaction scheme (I) is a known compound or can be produced, for example, by the procedure described in the Reference Examples hereinafter.

The basic compounds of the 1,3-benzoxazine derivatives of the general formula (I) can be converted into salts thereof by using acids. Suitable acids for this reaction are preferably those which can give pharmaceutically acceptable salts. They include inorganic acids such as hydrochloric acid, hydrobromic acid, phosphoric acid, sulfuric acid, nitric acid, sulfamic acid and the like, and organic acids such as acetic acid, tartaric acid, citric acid, fumaric acid, maleic acid, p-toluenesulfonic acid, methanesulfonic acid, glutamic acid and the like.

The desired compound (I) thus obtained can be isolated from a reaction mixture by conventional isolation and purification techniques, for example, extraction, concentration, neutralization, filtration, recrystallization, column (or thin layer) chromatography and the like.

The 1,3-benzoxazine derivatives and pharmaceutically acceptable salts thereof exhibit smooth muscle relaxation activity in animals, particularly, mammals (e.g., human being, monkey, dog, cat, rabbit, guinea pig, rat, mouse and the like), which is considered to be based on potassium channel opening (activating) activity, and they are useful as therapeutic and prophylactic agents against hypertension, asthma, congestive heart failure, angina pectoris, cerebrovascular contraction, arrhythmia, cerebral hemorrhage, dysmenorrhea, renal insufficiency, peripheral angiemphraxis, unstable bladder and anuresis, gastrointestinal disorder (particularly, irritable intestinal syndrome), epilepsia and the like.

The compounds of the present invention have low toxicity, can be absorbed well even through oral administration and have high stability. Therefor, when the compounds are used as the drug as described above, they can be safely administered orally or parenterally as they are, or in the form of a pharmaceutical composition prepared by admixing them with suitable pharmaceutically acceptable carriers, excipients, diluents and the like, for example, powders, granules, tablets, capsules including soft capsules and micro-capsules, liquids, injection preparations, suppositories and the like according to the conventional technique.

For example, 5 parts by weight of the compound (I) or a pharmaceutically acceptable salt thereof is admixed with 95 parts by weight of glucose to make a powdery preparation.

The dosage is varied depending upon patients, administration routes and conditions of diseases to be treated. However, for example, in the case of oral administration to an adult patient for the treatment of hypertension, normally, a dosage per one administration is about 0.001 to 10 mg/kg, preferably, about 0.001 to 0.2 mg/kg, more preferably, about 0.001 to 0.02 mg/kg. It is preferred that the administration is carried out about one to three times according to condition of diseases to be treated.

As described hereinabove, according to the present invention, the novel 1,3-benzoxazine derivatives which exhibit smooth muscles relaxation activities with few side effects of inhibitory activity on heart function and are useful as drugs can be provided.

The following Reference Examples, Examples and Experiments further illustrate the present invention in detail but are not to be construed to limit the scope thereof.

REFERENCE EXAMPLE 1

Preparation of Compound A-1

Acetyl chloride (43.3 g) was added dropwise with ice-cooling to a solution of 5-cyano-salicylic acid (29.0 g) and triethylamine (54.0 g) in dichloromethane (300 ml). After the addition was complete, the reaction mixture was stirred for 2 hours at ice-cooling temperature to room temperature. The solvent was distilled off under reduced pressure and the residue was extracted by addition of ethyl acetate and an aqueous potassium bisulfate solution. The ethyl acetate layer was washed with saturated saline solution, dried over anhydrous magnesium sulfate. The solvent was distilled off to obtain oil. This oil was dissolved in 1,2-dichloroethane (100 ml), and thionyl chloride (42.4 g) and dimethylformamide (0.5 ml) were added to the mixture, and the resulting mixture was heated under reflux for 1 hour. After air cooling, the solvent was distilled off under reduced pressure, and the residue was dissolved in tetrahydrofuran (100 ml). This solution was added with ice cooling to a mixed solution of aqueous ammonia (100 ml) and tetrahydrofuran (100 ml), and the mixture was stirred for 1 hour. An aqueous potassium bisulfate solution was added to the mixture to adjust to pH 2 to 3, and the mixture was extracted with ethyl acetate-tetrahydrofuran three times. The organic layers were combined and dried over anhydrous magnesium sulfate. The solvent was distilled off under reduced pressure to obtain crude 5-cyano-salicylamide.

To this crude product were added acetone (200 ml), 2,2-dimethoxypropane (100 ml) and p-toluenesufonic acid (6.6 g) and the mixture was heated under reflux for 16 hours. After air cooling, the solvent was distilled off. The residue was extracted by addition of ethyl acetate and an aqueous sodium bicarbonate solution. The ethyl acetate layer was washed with saturated saline solution, dried over anhydrous magnesium sulfate, and then the solvent was distilled off under reduced pressure. The residue was washed with isopropyl ether to obtain 6-cyano-2,2-dimethyl-3,4-dihydro-2H-1,3-benzoxazin-4-one (19.0 g) (Compound A-1). The physical properties are shown in Table 1.

According to the same manner as that described with respect to Compound A-1, Compounds A-2 to A-11, A-14 and A-16 to A-25 were prepared.

REFERENCE EXAMPLE 2

Preparation of Compound A-12

6-Iodo-2,2-dimethyl-3,4-dihydro-2H-1,3-benzoxazin-4-one (compound A-11, 10.0 g), thiophenol (17.2 g), potassium carbonate (10.0 g) and copper powder (1.0 g) were suspended in isoamyl alcohol (100 ml) and the suspension was heated to reflux for 3 hours under Ar. After air cooling, the reaction mixture was poured into water and extracted with ethyl acetate. The organic layer was successively washed with an aqueous sodium bicarbonate solution and saturated saline solution, dried over anhydrous magnesium sulfate, and the solvent was distilled off under reduced pressure. The residue was purified by column chromatography on silica gel eluting with ethyl acetate/hexane (2:1) to obtain 2,2-dimethyl-6-phenylthio-3,4-dihydro-2H-1,3-benzoxazin-4-one (2.67 g) (Compound A-12). The physical properties are shown in Table 1.

REFERENCE EXAMPLE 3

Preparation of Compound A-13 m-Chloroperbenzoic acid (70% purity, 4.64 g) was added with ice-cooling to a solution of 2,2-dimethyl-6-phenylthio-3,4-dihydro-2H-1,3-benzoxazin-4-one (2.24 g) in dichloromethane (50 ml) and the mixture was stirred for 30 minutes. The reaction mixture was poured into an aqueous sodium sulfite solution and the mixture was extracted by addition of ethyl acetate. The organic layer was successively washed with an aqueous sodium carbonate solution and saturated saline solution, dried over anhydrous magnesium sulfate, and the solvent was distilled off under reduced pressure. The residue was washed with isopropyl ether to obtain 2,2-dimethyl-6-phenylsulfonyl-3,4-dihydro-2H-1,3-benzoxazin-4-one (2.50 g) (Compound A-13). The physical properties are shown in Table 1.

REFERENCE EXAMPLE 4

Preparation of Compound A-15

Triethylamine (70 ml) was added to a mixture of Compound A-11 (7.0 g), trimethylsilylacetylene (11.1 g), palladium acetate (II) (0.49 g) and triphenylphosphine (1.2 g), and the mixture was stirred at 60° C. for 2 hours under an atmosphere of argon. After air cooling, the insoluble substance formed was filtered off and the filtrate was concentrated under reduced pressure. The residue was extracted by addition of ethyl acetate and sodium bicarbonate and the ethyl acetate layer was washed with saturated saline solution and dried over anhydrous magnesium sulfate. The solvent was concentrated under reduced pressure. The residue was crystallized from a small amount of ethyl acetate to obtain 2,2-dimethyl-6-trimethylsilylethynyl-2H-1,3-benzoxazin-4-one (3.4 g) (Compound A-15). The physical properties are shown in Table 1.

REFERENCE EXAMPLE 5

Phosphorous oxychloride (0.5 ml) was added with ice-cooling to dimethylformamide (10 ml) and the mixture was stirred for 10 minutes. To the mixture was added 6-cyano-2,2-dimethyl-3,4-dihydro-2H-1,3-benzoxazin-4-one (1.0 g), and the mixture was stirred with ice-cooling for 1 hour and then at room temperature for 2 hours. The mixture was extracted with addition of ethyl acetate and ice water. The ethyl acetate layer was successively washed with an aqueous sodium bicarbonate solution and saturated saline, dried over anhydrous magnesium sulfate. The solvent was distilled off under reduced pressure. Hexane was added to the residue and 4-chloro-6-cyano-2,2-dimethyl-2H-1,3-benzoxazine (0.41 g, mp. 124°–126° C.) was obtained by crystallization therefrom.

REFERENCE EXAMPLE 6

Preparation of Compound A-26

Methanol (2.1 liters) was added to 4-chlorosalicylic acid (60 g) and sodium acetate (120 g), and the mixture was cooled to −70° C. and stirred. To this mixture was added dropwise a solution of bromine (55.7 g) in methanol (557 ml) over 1.5 hours. After the reaction mixture was allowed to warm to room temperature, the solvent was distilled off under reduced pressure. The residue was acidified by addition of dilute hydrochloric acid (2 liters). The precipitate was filtered off, dissolved in ethyl acetate, dried over anhydrous magnesium sulfate, and the solvent was concentrated. The deposited crystals were recrystallized from hydrous ethanol to obtain 5-bromo-4-chlorosalicylic acid (43.8 g, mp. 208°–213° C.). According to the same manner as that described in Reference Example 1, by using this compound as the starting compound, 6-bromo-7-chloro-2,2-dimethyl-2H-1,3-benzoxazin-4-one (29.2 g) (Compound A-26) was obtained. The physical properties are shown in Table 1.

According to the same manner as that described with respect to Compound A-26, 4-bromosalicylic acid was converted into 4,5-dibromosalicylic acid (mp. 227°–232° C.), which was then converted into 6,7-dibromo-2,2-dimethyl-2H-1,3-benzoxazin-4-one (Compound A-27). Likewise, 4-fluorosalicylic acid was converted into 5-bromo-4-fluorosalicylic acid (mp. 203°–2050C.), which was then converted into 6-bromo-7-fluoro-2,2-dimethyl-2H-1,3-benzoxazin-4-one (Compound A-28). The physical properties of Compounds A-27 and A-28 are shown in Table 1.

TABLE 1

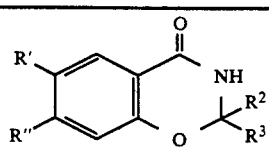

| Comp. No. | R' | R'' | $R^2$ | $R^3$ | Comp. formula | m.p. (°C.) |
|---|---|---|---|---|---|---|
| A-1 | CN | H | Me | Me | $C_{11}H_{10}N_2O_2$ | 208~212 |
| A-2 | H | H | Me | Me | $C_{10}H_{11}NO_2$ | 139~141 |
| A-3 | Me | H | Me | Me | $C_{11}H_{13}NO_2$ | 164~165 |
| A-4 | Br | H | Me | Me | $C_{10}H_{10}BrNO_2$ | 177~179 |
| A-5 | Cl | H | Me | Me | $C_{10}H_{10}ClNO_2$ | 153.5~154.5 |
| A-6 | $CO_2Me$ | H | Me | Me | $C_{12}H_{13}NO_4$ | 188~192 |
| A-7 | Bz | H | Me | Me | $C_{17}H_{15}NO_3$ | 232~234 |

TABLE 1-continued

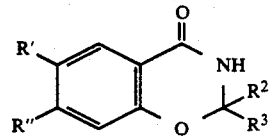

| Comp. No. | R' | R" | R2 | R3 | Comp. formula | m.p. (°C.) |
|---|---|---|---|---|---|---|
| A-8 | 4-Cl—Bz | H | Me | Me | $C_{17}H_{14}ClNO_3$ | 206~207 |
| A-9 | H | Me | Me | Me | $C_{11}H_{13}NO_2$ | 168~171 |
| A-10 | $CO_2Bu^i$ | H | Me | Me | $C_{15}H_{19}NO_4$ | 158~161 |
| A-11 | I | H | Me | Me | $C_{10}H_{10}INO_2$ | 148~149 |
| A-12 | PhS | H | Me | Me | $C_{16}H_{15}NO_2S$ | 162.5~163.5 |
| A-13 | $PhSO_2$ | H | Me | Me | $C_{16}H_{15}NO_4S$ | 201.5~202.5 |
| A-14 | Bz | Me | Me | Me | $C_{18}H_{17}NO_3$ | 250-251 |
| A-15 | $Me_3SiC\equiv C$ | H | Me | Me | $C_{15}H_{19}NO_2Si$ | 194-195 |
| A-16 | Ac | H | Me | Me | $C_{12}H_{13}NO_3$ | 161.5-162.5 |
| A-17 | H | EtO | Me | Me | $C_{12}H_{15}NO_3$ | 174-177 |
| A-18 | $CF_3O$ | H | Me | Me | $C_{11}H_{10}F_3NO_3$ | 125-128 |
| A-19 | MeO | H | Me | Me | $C_{11}H_{13}NO_3$ | 133-136 |
| A-20 | $CF_3$ | H | Me | Me | $C_{11}H_{10}F_3NO_2$ | 171-172.5 |
| A-21 | $C_2F_5$ | H | Me | Me | $C_{12}H_{10}F_5NO_2$ | 165-167 |
| A-22 | Cl | Cl | Me | Me | $C_{10}H_9Cl_2NO_2$ | 229-231 |
| A-23 | Et | H | Me | Me | $C_{12}H_{15}NO_2$ | 129-131 |
| A-24 | —CH=CH—CH=CH— | | Me | Me | $C_{14}H_{13}NO_2$ | 225-227 |
| A-25 | H | Cl | Me | Me | $C_{10}H_{10}ClNO_2$ | 160-163 |
| A-26 | Br | Cl | Me | Me | $C_{10}H_9BrClNO_2$ | 230-233 |
| A-27 | Br | Br | Me | Me | $C_{10}H_9Br_2NO_2$ | 247-251 |
| A-28 | Br | F | Me | Me | $C_{10}H_9BrFNO_2$ | 207-210 |

REFERENCE EXAMPLE 7

Bromine (15.9 ml) was added to a solution of 4-trifluoromethylphenol (50 g) in dichloromethane (300 ml) at room temperature and the mixture was stirred for 38 hours. The reaction mixture was successively washed with aqueous sodium bisulfite solution and saturated saline solution, dried over anhydrous magnesium sulfate, and the solvent was distilled off to obtain crude 2-bromo-4-trifluoromethylphenol (78.5 g) as oil. N,N-dimethylformamide (250 ml) was added to the crude product and copper cyanide (I) (27.6 g), and the mixture was heated to reflux for 2 hours under Ar. This hot reaction mixture was poured into a solution of ferric chloride hexahydrate (137.5 g) and hydrochloric acid (35 ml) in water (400 ml), and the mixture was stirred for 30 minutes. The mixture was extracted with ethyl acetate, and the ethyl acetate was successively washed with dilute hydrochloric acid and saturated saline solution, and dried over anhydrous magnesium sulfate. The solvent was distilled off under reduced pressure. The residue was purified by column chromatography on silica gel eluting with ethyl acetate/hexane to obtain 2-cyano-4-trifluoromethylphenol (34.6 g, mp. 149.5°-151° C.).

REFERENCE EXAMPLE 8

Methanol (100 ml) was added to sodium acetate (1.97 g) and 5-chloro-2-cyanophenol (1.84 g, mp. 155°-157° C.) which was synthesized according to a known method. The mixture was allowed to cool to −78° C., and to the solution was added dropwise a solution of bromine (1.53 g) in methanol (25 ml). After stirring at −78° C. for 30 minutes, the solvent was distilled off under reduced pressure, and ethyl acetate and aqueous potassium bisulfate solution were added to the residue. The ethyl acetate layer was washed with saturated saline solution, dried over anhydrous magnesium sulfate and the solvent was distilled off. The residue was purified by column chromatography on silica gel eluting with ethyl acetate/hexane to obtain 4-bromo-5-chloro-2-cyanophenol (0.53 g, mp. 229°-231° C. (dec.)).

REFERENCE EXAMPLE 9

Anhydrous tetrahydrofuran (50 ml) was added to 5-bromo-4-chlorosalicylic acid (11.0 g) and lithium hydroxide monohydrate (1.84 g) and the mixture was heated under reflux for 1 hour. The reaction mixture was concentrated to dryness under reduced pressure and the residue was then dissolved in anhydrous tetrahydrofuran (50 ml). Molecular sieves 4A was added to the mixture and the mixture was allowed to stand overnight (hereinafter referred to as as liquid A). A solution of 2-bromopyridine (10.4 ml) in anhydrous tetrahydrofuran (136 ml) was cooled to −78° C. and a solution (68 ml) of 1.6M n-butyllithium in hexane was added dropwise over 30 minutes to the cooled solution. After stirring for 10 minutes, liquid A was added dropwise. After completion of the addition, the mixture was allowed to warm slowly to −10° C. over 40 minutes, and further stirred at −10° C. to −5° C. for 1 hour. The reaction was quenched by adding methanol (10 ml) and the mixture was extracted with addition of saturated ammonium chloride solution and ethyl acetate. The organic layer was washed with saturated saline solution and dried over anhydrous magnesium sulfate. The solvent was distilled off and the residue was subjected to silica gel column chromatography and eluted with hexane/ethyl acetate. The resulting crystals were washed with hexane to obtain 5-bromo-4-chloro-2-hydroxyphenyl 2-pyridyl ketone (5.44 g).

EXAMPLE 1

Preparation of Compound 1

Dichloromethane (20 ml) was added to 6-cyano-2,2-dimethyl-3,4-dihydro-2H-1,3-benzoxazin-4-one (0.80 g) and the mixture was cooled to −78° C. under an argon atmosphere. To the mixture was added trifluoromethanesulfonic anhydride (1.0 ml) followed by 2,6-lutidine (1.0 ml) and the mixture was stirred for 10 minutes.

The mixture was allowed to warm to 0° C. and stirred for additional 30 minutes. Then, the mixture was extracted by addition of ethyl acetate and ice water. The organic layer was successively washed with an aqueous sodium bisulfate solution, an aqueous sodium bicarbonate solution and saturated saline solution and dried over anhydrous magnesium sulfate. The solvent was distilled off under reduced pressure and the residue was dissolved in anhydrous tetrahydrofuran (5 ml) to obtain a triflate solution.

On the other hand, a solution (6.8 ml) of n-butyllithium (1.6M) in hexane was added dropwise at −78° C. under an argon atmosphere to a solution of 2-bromopyridine (1.58 g) in anhydrous tetrahydrofuran (20 ml). After 30 minutes, a solution of zinc chloride (1.36 g) in anhydrous tetrahydrofuran (10 ml) was added, and the mixture was stirred at −78° C. for 15 minutes and then under ice-cooling for 15 minutes. Tetrakis(triphenylphosphine)palladium (O) (0.30 g) and the above triflate solution were added. The mixture was allowed to warm to room temperature and stirred for additional 18 hours, and aqueous saturated sodium bicarbonate solution was added. The insoluble substance formed was filtered off and the filtrate was extracted with ethyl acetate twice. The organic layers were combined, washed with saturated saline solution, dried over anhydrous magnesium sulfate, and concentrated under reduced pressure. The residue was purified by column chromatography on silica gel and eluted with hexane/ethyl acetate (1:5) to (1:2) to obtain 6-cyano-2,2-dimethyl-4-(2-pyridyl)-2H-1,3-benzoxazine (0.28 g) (Compound 1). Likewise, Compounds 2 to 8, 10 13, 30, 31, 39, 44, 50, 54, 55, 61, 68, 70, 74, 76, 78, 80, 82, 84, 88, 92 and 94 were prepared.

The physical properties and spectrum data of these compounds and compounds obtained in Examples hereinafter are shown in Table 2.

EXAMPLE 2

Preparation of Compound 16

According to the same manner as that described in the preparation of Compound 1 in Example 1, 6-cyano-2,2-dimethyl-4-(1-phenylsulfonyl-indol-2-yl)-2H-1,3-benzoxazine (Compound 16) was obtained except that N-phenylsulfonylindole was used instead of 2-bromopyridine.

Likewise, Compounds 14 and 17 were prepared.

EXAMPLE 3

Preparation of Compound 15

According to the same manner as that described in the preparation of Compound 1 in Example 1, 6-cyano-2,2-dimethyl-4-(1-methyl-2-oxopyrrolidin-3-yl)-2H-1,3-benzoxazine (Compound 15) was obtained except that N-methylpyrrolidone and a solution of 1.6M lithium diisopropylamide in a mixed solvent of tetrahydrofuran and hexane were used instead of 2-bromopyridine and the solution of 1.6M n-butyl lithium in hexane, respectively.

EXAMPLE 4

Preparation of Compound 33

According to the same manner as that described in the preparation of compound 1 in Example 1, 6-cyano-2,2-dimethyl-4-[4-trimethylsilyl-3-(2-trimethylsilylethoxymethyloxy)pyridine-2-yl]-2H-1,3-benzoxazine (Compound 33) was obtained except that 4-trimethylsilyl-3-(2-trimethylsilylethoxymethyloxy)pyridine, a solution of 1.6M t-butyllithium in pentane and diethyl ether were used instead of 2-bromopyridine and the solution of 1.6M n-butyllithium in hexane and tetrahydrofuran, respectively.

EXAMPLE 5

Preparation of Compound 9

Aqueous 2N sodium hydroxide solution (6 ml) and 30% hydrogen peroxide solution (8 ml) were added dropwise over 20 minutes to a solution of 6-cyano-2,2-dimethyl-4-(2-pyridyl)-2H-1,3-benzoxazine (0.40 g) in tetrahydrofuran(16 ml). The mixture was stirred at room temperature for 40 minutes. The reaction mixture was extracted by addition of ethyl acetate. The organic layer was successively washed with an aqueous sodium bicarbonate solution, an aqueous sodium bisulfite and saturated saline and dried over anhydrous magnesium sulfate. The solvent was distilled off under reduced pressure. The residue was washed with diethyl ether to obtain 6-carbamoyl-2,2-dimethyl-4-(2-pyridyl)-2H-1,3-benzoxazine (0.30 g) (compound 9).

EXAMPLE 6

Preparation of Compound 11

2,2-Dimethyl-4-(2-pyridyl)-2H-1,3-benzoxazine (0.50 g) was dissolved in acetic acid (1 ml) and to the solution was added conc. sulfuric acid (3 ml) with ice-cooling. Conc. nitric acid (0.2 ml) was then added to the mixture, and the mixture was stirred for 10 minutes with ice-cooling. The reaction mixture was added slowly to a thoroughly cooled mixture of an aqueous 5N sodium hydroxide solution (50 ml) and saturated bicarbonate solution (20 ml) to quench the reaction. The mixture was extracted by addition of ethyl acetate. The mixture was successively washed with an aqueous sodium bicarbonate solution and saturated saline solution and dried over anhydrous magnesium sulfate. The solvent was distilled off under reduced pressure and the residue was crystallized from hexane to obtain 6-nitro-2,2-dimethyl-4-(2-pyridyl)-2H-1,3-benzoxazine (0.58 g) (Compound 11).

Likewise, Compounds 48, 57, 66 and 72 were prepared.

EXAMPLE 7

Preparation of Compound 12

Molecular sieves 5A (5 g) and tertrabutylammonium fluoride trihydrate (3.2 g) were added to a solution of 6-cyano-2,2-dimethyl-4-[4-trimethylsilyl-3-(2-trimethylsilylethoxymethyloxy)pyridin-2-yl]-2H-1,3-benzoxazine (2.5 g) in tetrahydrofuran (20 ml), and the mixture was heated under reflux for 30 minutes. After air-cooling, the mixture was extracted by addition of ethyl acetate. The organic layer was washed with saturated saline solution, the solvent was distilled off under reduced pressure and the residue was crystallized from ethyl acetate to obtain 6-cyano-2,2-dimethyl-4-(3-hydroxypyridin-2-yl)-2H-1,3-benzoxazine (0.19 g) (Compound 12).

EXAMPLE 8

Preparation of Compound 18

Methyliodide (2 ml) was added to a solution of 6-cyano-2,2-dimethyl-4-(2-pyridyl)-2H-1,3-benzoxazine (0.20 g) in acetonitrile (14 ml) and the mixture was heated under reflux for 7 hours. After air-cooling, the solvent was distilled off under reduced pressure and the residue was crystallized from diethyl ether to obtain 2-(6-cyano-2,2-dimethyl-2H-1,3-benzoxazin-4-yl)-1-methylpyridinium iodide (0.29 g) (Compound 18).

EXAMPLE 9

Preparation of Compound 19

To a suspension of sodium hydride (0.24 g) in dimethylformamide (10 ml) was added 2-cyanoiminoimidazolidine (1.00 g) with ice-cooling and the mixture was stirred at room temperature for 10 minutes. Then, 4-chloro-6-cyano-2,2-dimethyl-2H-1,3-benzoxazine (1.09 g) was added to the mixture and the mixture was stirred at room temperature for additional 5 hours. The reaction mixture was extracted with addition of ethyl acetate and an aqueous sodium bicarbonate solution. The ethyl acetate layer was successively washed with water and aqueous saturated saline solution and dried over anhydrous magnesium sulfate, the solvent was distilled off under reduced pressure and the residue was crystallized from ether to obtain 6-cyano-4-(2-cyanoiminoimidazoline-1-yl)-2,2-dimethyl-2H-1,3-benzoxazine (0.23 g) (Compound 19).

Likewise, Compound 34 was prepared.

EXAMPLE 10

Preparation of Compound 20 m-Chloroperbenzoic acid (70% purity, 0.75 g) was added at −20° C. to a solution of 6-cyano-2,2-dimethyl-4-(2-pyridyl)-2H-1,3-benzoxazine (0.40 g) in dichloromethane (10 ml) and the mixture was stirred for 30 hours. The reaction mixture was extracted by addition of an aqueous sodium sulfite solution and ethyl acetate. The organic layer was successively washed with aqueous sodium carbonate and saturated saline solution and dried over anhydrous magnesium sulfate and the solvent was distilled off under reduced pressure. The residue was subjected to column chromatography on silica gel, and it was crystallized from isopropyl ether to obtain 2-(6-cyano-2,2-dimethyl-2H-1,3-benzoxazin-4-yl)pyridine N-oxide (0.09 g) (Compound 20). Likewise, Compounds 21 to 29, 32, 36, 38, 43, 45, 47, 49, 51, 56, 58, 60, 63, 65, 67, 69, 71, 73, 75, 77, 79, 81, 83, 85, 87, 89, 91, 93, 95, 97, 106, 107, 108, 109, 110, 117, 118, 119 and 144 were prepared.

EXAMPLE 11

Preparation of Compound 35

Compound 2 (1.17 g) was added at room temperature to a mixture of chlorosulfuric acid (5.83 g) and chloroform (50 ml) and the mixture was heated to 80° C. and heated under reflux for 3 hours. The reaction mixture was ice-cooled and added dropwise to conc. aqueous ammonia solution, and the mixture was stirred for 1 hour. The reaction mixture was extracted by addition of ethyl acetate and the organic layer was dried over anhydrous magnesium sulfate, and then the solvent was distilled off and the residue was crystallized from isopropyl ether to obtain 6-aminosulfonyl-2,2-dimethyl-4-(2-pyridyl)-2H-1,3-benzoxazine (0.16 g) (Compound 35).

EXAMPLE 12

Preparation of Compound 40

Compound 39 (0.60 g) was dissolved in a mixture of tetrahydrofuran (20 ml) and water (10 ml). Sodium periodate (1.5 g) was added to the mixture at room temperature and the mixture was stirred for 4 hours. The reaction mixture was extracted with ethyl acetate twice. The organic layers were combined, washed successively with water and saturated saline solution and dried over anhydrous magnesium sulfate and the solvent was distilled off. The residue was purified by column chromatography on silica gel, and crystallized from isopropyl ether to obtain 6-cyano-2,2-dimethyl-4-(2-methylsulfinylphenyl)-1,3-benzoxazine (0.38 g) (Compound 40)

Likewise, Compound 42 was prepared

EXAMPLE 13

Preparation of Compound 41

According to the same manner as that described in the preparation of Compound 1 in Example 1, 6-cyano-2,2-dimethyl-4-(3,4-dihydro-2H-6-thiopyranyl)-2H-1,3-benzoxazine (Compound 41) was obtained except that 3,4-dihydro-2H-thiopyran (bp. 45°–50° C./20 mmHg) was used instead of 2-bromopyridine.

EXAMPLE 14

Preparation of Compound 46

Sodium acetate (0.41 g) was added to a solution of Compound 10 (0.50 g) in ethyl acetate (10 ml), and the mixture was cooled to −40° C. A solution of bromine (0.32 g) in ethyl acetate (3 ml) was added dropwise to the mixture over 10 minutes and the mixture was stirred for 15 minutes. The reaction mixture was poured into an aqueous potassium carbonate solution. The ethyl acetate layer was washed with saturated saline solution and dried over anhydrous magnesium sulfate and the solvent was distilled off under reduced pressure. The residue was purified by chromatography on silica gel to obtain 6-bromo-2,2,7-trimethyl-4-(2-pyridyl)-2H-1,3-benzoxazine (0.47 g) (Compound 46).

EXAMPLE 15

Preparation of Compound 52

Potassium carbonate (8 mg) was added to a solution of Compound 50 (100 mg) in methanol (1 ml) and the mixture was stirred at room temperature for 1.5 hours under an argon atmosphere. Methanol was distilled off under reduced pressure. An aqueous sodium bicarbonate solution was added to the residue and the mixture was extracted with ethyl acetate. The ethyl acetate layer was washed with saturated saline solution and dried over anhydrous magnesium sulfate, and the solvent was distilled off. The residue was purified by chromatography on silica gel to obtain 6-ethynyl-2,2-dimethyl-4-(2-pyridyl)-2H-1,3-benzoxzine (42 mg) (Compound 52).

Likewise, Compound 53 was prepared.

EXAMPLE 16

Preparation of Compound 59

Sodium acetate (1.5 g) was added to a solution of Compound 10 (1.5 g) in acetic acid (20 ml) and the mixture was cooled to 5° C. A solution of bromine (2.0 g) in acetic acid (20 ml) was added dropwise over 15 minutes. Then, the mixture was allowed to warm and stirred at room temperature for 3 hours. Water was added to the reaction mixture and the resulting mixture was extracted with ethyl acetate. The organic layer was successively washed with aqueous sodium bicarbonate solution and saturated saline solution and dried with anhydrous magnesium sulfate and the solvent was distilled off. The residue was purified by chromatography on silica gel to obtain 6,8-dibromo-2,2,7-trimethyl-4-(2-pyridyl)-2H-1,3-benzoxazine (0.33 g) (Compound 59).

EXAMPLE 17

Preparation of Compound 37

According to the same manner as that described in the preparation of Compound 1 in Example 1, 6-cyano-4-(3-ethoxy-2-pyridyl)-2,2-dimethyl-2H-1,3-benzoxazine (Compound 37) was obtained except that 3-ethoxypyridine (bp. 90°-95° C./20 mmHg) and N,N,N',N'-tetramethylethylenediamine were used instead of 2-bromopyridine.

Likewise, Compounds 120 and 121 were prepared. Also, Compounds 122 and 123 were prepared from 3-methoxypyridine (b.p. 77°-78° C./18 mmHg).

EXAMPLE 18

Preparation of Compound 62

Sodium acetate (0.84 g) was added to a solution of Compound 61 (0.84 g) in methanol (25 ml) and the mixture was cooled to −60° C. A solution of bromine (0.48 g) in methanol (10 ml) was added dropwise to the resulting mixture. Then, the mixture was allowed to warm and stirred at room temperature for 2 hours. The reaction mixture was concentrated under reduced pressure and the residue was extracted by addition of ethyl acetate and aqueous sodium bicarbonate solution. The ethyl acetate layer was washed with saturated saline solution and dried over anhydrous magnesium sulfate and the solvent was distilled off. The crude product thus obtained was washed with hexane to obtain 6-bromo-7-ethoxy-2,2-dimethyl-4-(2-pyridyl)-2H-1,3-benzoxazine (0.64 g) (Compound 62).

EXAMPLE 19

Preparation of Compound 64

Cuprous cyanide (1.1 g) was added to a solution of Compound 46 (2.0 g) in dimethylformamide (5 ml) and the mixture was heated under reflux for 23 hours. The reaction mixture was air-cooled. The mixture was then added to a solution of sodium cyanide (2.2 g) in water (6.5 ml), and the mixture was stirred for 15 minutes. The mixture was extracted with ethyl acetate, successively washed with aqueous 5% sodium cyanide solution and saturated saline solution and dried over anhydrous magnesium sulfate. The solvent was distilled off. The resulting crude product was washed with ether/isopropyl ether to obtain 6-cyano-2,2,7-trimethyl-4-(2-pyridyl)-2H-1,3-benzoxazine (0.35 g) (Compound 64).

Likewise, Compounds 86 and 90 were prepared.

EXAMPLE 20

Preparation of Compound 96

According to the same manner as that described in the preparation of Compound 1 in Example 1, 6-cyano-2,2-dimethyl-4-(3-pyridyl)-2H-1,3-benzoxazine (compound 96) was obtained except that a solution of 3-bromopyridine in anhydrous diethyl ether and a solution of zinc chloride in anhydrous diethyl ether were used instead of the solution of 2-bromopyridine in anhydrous tetrahydrofuran and the solution of zinc chloride in anhydrous tetrahydrofuran, respectively.

Likewise, Compound 98 was prepared.

EXAMPLE 21

Preparation of Compound 2

To 2-bromophenol (1.73 g) was added 2-methoxypropene (0.87 g), and the mixture was stirred at room temperature for 30 minutes. Excess 2-methoxypropene was distilled off under reduced pressure and anhydrous tetrahydrofuran (20 ml) was added to the residue. The mixture was cooled to −78° C. and 1.6M n-butyllithium solution (6.9 ml) in hexane was added dropwise under Ar. The mixture was stirred at −78° C. for 20 minutes. Then, a solution of 2-cyanopyridine (1.04 g) in anhydrous tetrahydrofuran (5 ml) was added dropwise and the mixture was stirred at −78° C. for 1 hour. The reaction was quenched by adding an aqueous sodium bicarbonate solution and the mixture was extracted with ethyl acetate. The organic layer was washed with saturated saline solution and dried over anhydrous magnesium sulfate and the solvent was distilled off. Ammonium acetate (5 g) and 2,2-dimethoxypropane (30 ml) were added to the residue and the mixture was heated under reflux for 1 hour. The solvent was distilled off under reduced pressure and the residue was extracted by addition of ethyl acetate and aqueous sodium bicarbonate solution. The ethyl acetate layer was washed with saturated saline solution and dried over anhydrous magnesium sulfate. The solvent was distilled off. The residue was subjected to column chromatography on silica gel and eluted with ethyl acetate/hexane to obtained 2,2-dimethyl-4-(2-pyridyl)-2H-1,3-benzoxazine (1.0 g) (Compound 2).

EXAMPLE 22

Preparation of Compound 4

Methanol (25 ml) was added to a mixture of Compound 2 (1.19 g) and sodium acetate (0.82 g). The mixture was cooled to −40° C. and bromine (0.96 g) was added to the mixture. After completion of the addition, the mixture was warmed and the mixture was stirred at 5° to 8° C. for 18 hours. The reaction was quenched by adding aqueous sodium sulfite solution, and the methanol was distilled off. The residue was extracted with ethyl acetate. The extract was successively washed with aqueous sodium bicarbonate solution and saturated saline solution and dried over anhydrous magnesium sulfate. The solvent was distilled off. The residue was subjected to column chromatography on silica gel and eluted with ethyl acetate/hexane to obtain 6-bromo-2,2-dimethyl-4-(2-pyridyl)-2H-1,3-benzoxazine (0.41 g) (Compound 4).

EXAMPLE 23

Preparation of Compound 68

A solution of 4-trifluoromethoxyphenol (4.0 g) in methanol (50 ml) was cooled to −78° C. To the solution was added a solution of bromine (3.59 g) in methanol (20 ml). The mixture was stirred for 1 hour at −78° C. and then the reaction was quenched by adding aqueous sodium sulfite solution. The methanol was distilled off under reduced pressure. The residue was extracted with ethyl acetate, washed with saturated saline solution and dried over anhydrous magnesium sulfate and the solvent was distilled off. According to the same manner as that described in Example 21, 6-trifluoromethoxy-2,2-dimethyl-4-(2-pyridyl)-2H-1,3-benzoxazine (1.3 g)

(Compound 68) was obtained from the resulting crude 2-bromo-4-trifluoromethoxyphenol.

EXAMPLE 24

Preparation of Compound 74

A solution of 2-bromopyridine (0.47 g) in anhydrous tetrahydrofuran (5 ml) was cooled to −78° C. and 1.6M n-butyllithium in hexane (2.1 ml) was added dropwise under an argon atmosphere. The mixture was stirred for 30 minutes. Then, a solution of 2-cyano-4-trifluoromethylphenol (0.19 g) in anhydrous tetrahydrofuran (5 ml) was added to the reaction mixture and the resulting mixture was stirred at −78° C. for an additional 1 hour. The reaction was quenched by adding acetic acid (0.18 g) to the reaction mixture and the solvent was distilled off under reduced pressure. Ammonium acetate (2 g) and 2,2-dimethoxypropane (5 ml) were added to the residue and the mixture was heated under reflux for 3 hours. The solvent was distilled off and the residue was extracted by addition of ethyl acetate and aqueous sodium bicarbonate solution. The ethyl acetate layer was washed with saturated saline solution and dried over anhydrous magnesium sulfate and the solvent was distilled off. The residue was purified by column chromatography on silica gel to obtain 6-trifluoromethyl-2,2-dimethyl-4-(2-pyridyl)-2H-1,3-benzoxazine (0.19 g) (Compound 74).

EXAMPLE 25

Preparation of Compound 88

A solution of 2-bromopyridine (316 mg) in anhydrous tetrahydrofuran (5 ml) was cooled to −78° C. and 1.6M n-butyllithium solution (1.3 ml) in hexane was added dropwise to the solution under an argon atmosphere. The resulting mixture was stirred for 30 minutes. Then, a solution of 2.82M magnesium bromide in benzene/ether (0.78 ml) was added and the mixture was stirred at −78° C. for 30 minutes and at 5° C. for 15 minutes. A solution of 5-bromo-4-chloro-2-cyanophenol (116 mg) in anhydrous tetrahydrofuran (3 ml) was then added and the resultant mixture was stirred at 5° C. for 30 minutes. The solvent was distilled off under reduced pressure and ammonium acetate (2 g) and 2,2-dimethoxypropane (5 ml) were added. The mixture was heated under reflux for 3 hours. The solvent was distilled off and the residue was extracted with water and ethyl acetate. The ethyl acetate layer was successively washed with aqueous sodium bicarbonate solution and saturated saline solution and dried over anhydrous magnesium sulfate. The solvent was distilled off. The residue was purified by column chromatography on silica gel to obtain 6-bromo-7-chloro-2,2-dimethyl-4-(2-pyridyl)-2H-1,3-benzoxazine (35 mg) (Compound 88).

EXAMPLE 26

Preparation of Compound 82

To acetone (3 ml) saturated with ammonia were added 3-hydroxy-2-naphthyl 2-pyridyl ketone (30 mg, mp.104°-109° C.), ammonium chloride (6 mg) and anhydrous calcium sulfate (30 mg) at room temperature. The mixture was stirred for 4 hours at 85° C. in a sealed tube. The insoluble substance in the reaction mixture was filtered off. Aqueous saturated ammonium chloride solution was added to the filtrate and the mixture was extracted with ethyl acetate. The organic layer was washed with saturated sodium chloride solution and dried over anhydrous magnesium sulfate. The solvent was distilled off. The residue was purified by column chromatography on silica gel and eluted with ethyl acetate/hexane to obtain 2,2-dimethyl-4-(2-pyridyl)-2H-naphtho[2,3-e][1,3]oxazine (18 mg) (Compound 82).

EXAMPLE 27

Preparation of Compound 88

Into a sealed tube were placed 5-bromo-4-chloro-2-hydroxylphenyl 2-pyridyl ketone (30 g), ammonium chloride (30 g), anhydrous calcium sulfate (60 g) and acetone (500 ml) and the mixture was thoroughly mixed. Then, a solution (300 ml) of saturated ammonia in acetone was added with ice-cooling to the resultant mixture. The mixture was stirred at 80° C. for 7 hours. After air-cooling, sodium bicarbonate (60 g) was added and the mixture was stirred for 1 hour. The insoluble substance was filtered off and washed with ethyl acetate. The filtrate was concentrated under reduced pressure. The residue was subjected to silica gel column chromatography and eluted with hexane/ethyl acetate. The crude crystals thus obtained were washed with cold hexane to obtain 6-bromo-7-chloro-2,2-dimethyl-4-(2-pyridyl)-2H-1,3-benzoxazine (15.2 g) (Compound 88).

EXAMPLE 28

Preparation of Compound 89

To a solution of Compound 88(10.0 g) in dichloromethane (130 ml) was added 70% m-chloroperbenzoic acid (20.0 g) at 0° C. and the mixture was stirred at 2° to 4° C. for 5 hours. A solution of sodium sulfite (32 g) in water (130 ml) was added slowly and stirred for 1 hour with ice-cooling. The organic layer was separated, washed successively with 5% aqueous sodium carbonate solution and saturated saline solution and dried over anhydrous magnesium sulfate. The solvent was distilled off and the residue was purified by chromatography on silica gel and crystallized from diethyl ether to obtain 2-(6-bromo-7-chloro-2,2-dimethyl-2H-1,3-benzoxazin-4-yl)pyridine 1-oxide (2.7 g) (Compound 89).

Likewise, Compounds 124 to 133 were prepared.

EXAMPLE 29

Preparation of Compound 99

To 2,4-dibromophenol (8.76 g) was added 2-methoxypropene (3.0 g) and the mixture was stirred at room temperature for 1 hour. The reaction mixture was then concentrated under reduced pressure. The residue was dissolved in anhydrous diethyl ether (70 ml) and a solution (23 ml) of 1.6M butyllithium in hexane was added dropwise at −78° C. over 15 minutes under an argon atmosphere. After 20 minutes, a solution of 4-cyanopyridine (3.32 g) in anhydrous tetrahydrofuran (14 ml) was added dropwise over 10 minutes. After completion of the addition, stirring was continued and the mixture was allowed to warm slowly to room temperature over 80 minutes. The reaction mixture was concentrated under reduced pressure. Ammonium acetate (15.0 g) and 2,2-dimethoxypropane (80 ml) were added and the mixture was heated under reflux for 6 hours. After air-cooling, the reaction mixture was concentrated under reduced pressure and the residue was extracted by addition of ethyl acetate and water. The ethyl acetate layer was washed with successively with aqueous saturated sodium bicarbonate solution and saturated saline solution and dried over anhydrous magnesium sulfate. The solvent was distilled off and the residue was purified by silica gel column chromatography and eluted with ethyl acetate/hexane to obtain 6-bromo-2,2-dimethyl-4-(4-pyridyl)-2H-1,3-benzoxazine (3.94 g) (Compound 99).

Likewise, Compound 100 was prepared from 2-cyano-4-methylpyridine (m.p. 89°–91° C.), Compound 101 was prepared from 2-benzyloxybenzonitrile (m.p. 74°–75° C.), Compound 102 was prepared from 1-cyanoisoquinoline (m.p. 87° C.), Compound 103 was prepared from 2-cyanoquinoline (m.p. 96°–98° C.), Compound 104 was prepared from 2-cyanopyrimidine (m.p. 40°–41° C.), Compound 134 was prepared from 2-cyano-3-methoxypyridine (m.p. 111°–112° C.), Compound 135 was prepared from 3-chloro-2-cyanopyridine (m.p. 85°–86° C.), Compound 136 was prepared from 2-cyano-3-methylpyridine (m.p. 82°–85° C.) and Compound 137 was prepared from 2-cyano-3-(2-trimethylsilylethoxymethyloxy)pyridine (oil) which was prepared from 2-cyano-3-hydroxypyridine (m.p. 211°–212° C. (dec.)) according to a known method.

EXAMPLE 30

Preparation of Compound 105

A solution (13.8 ml) of 1.6M n-butyllithium in hexane was added dropwise to a solution of 1,3-dithian (1.5 g) in anhydrous tetrahydrofuran (35 ml) at −78° C. under an argon atmosphere over 10 minutes. After stirring for 30 minutes, a solution of 5-bromo-2-(2-methoxy-2-methylethoxy)benzonitrile, which was prepared from 4-bromo-2-cyanophenol (m.p. 148°–150° C., 2.48 g) and 2-methoxypropene (1.1 g) according to the same manner as described in Example 29, in anhydrous tetrahydrofuran (5 ml) was added to the mixture. The mixture was treated in the same manner as that in Example 29 to obtain 6-bromo-2,2-dimethyl-4-(1,3-dithian-2-yl)-2H-1,3-benzoxazine (0.90 g) (Compound 105).

EXAMPLE 31

Preparation of Compound 111

A solution of sodium periodate (430 mg) in water (6 ml) was added to a solution of Compound 105 (600 mg) in methanol (18 ml) and the mixture was stirred at room temperature for 18 hours. The methanol was distilled off under reduced pressure and the residue was extracted with ethyl acetate. The ethyl acetate layer was washed with aqueous saline solution and dried over anhydrous magnesium sulfate. The solvent was distilled off. The residue was purified by chromatography on silica gel to obtain a solid. The solid was recrystallized from ethyl acetate to obtain 2-(6-bromo-2,2-dimethyl-2H-1,3-benzoxazin-4-yl)-1,3-dithian-1-oxide (331 mg) (Compound 111).

EXAMPLE 32

Preparation of Compound 112

Compound 9 (2.95 g), di-t-butyl-dicarbonate (5.73 g) and 4-dimethylaminopyridine (0.13 g) were dissolved in anhydrous tetrahydrofuran (100 ml) and the mixture was heated under reflux for 40 minutes. After air-cooling, the solvent was distilled off and the residue was purified by chromatography on silica gel to obtain 6-[N,N-(di-t-butoxycarbonyl)carbamoyl]-2,2-dimethyl-4-(2-pyridyl)-2H-1,3-benzoxazine (3.93 g) (Compound 112).

EXAMPLE 33

Preparation of Compound 113

Aqueous 4N sodium hydroxide (14.5 ml) was added to a solution of Compound 112 (3.50 g) in methanol (60 ml) and the mixture was stirred at room temperature for 20 minutes. The reaction mixture was concentrated under reduced pressure and the residue was extracted by addition of water and diethyl ether. The water was acidified to pH 5 by addition of potassium bisulfate and then ethyl acetate was added to the mixture. The ethyl acetate layer was washed with saturated saline solution and dried over anhydrous magnesium sulfate. The solvent was distilled off and the residue was crystallized from hexane to obtain 6-carboxy-2,2-dimethyl-4-(2-pyridyl)-2H-1,3-benzoxazine (0.79 g) (Compound 113).

EXAMPLE 34

Preparation of Compound 6

A solution of diazomethane in diethyl ether was added to a solution of Compound 113 (0.70 g) in tetrahydrofuran (5 ml) at room temperature until the starting material disappeared. The reaction mixture was concentrated under reduced pressure. The residue was purified by silica gel column chromatography to obtain 6-methoxycarbonyl-2,2-dimethyl-4-(2-pyridyl)-2H-1,3-benzoxazine (0.49 g) (Compound 6).

EXAMPLE 35

Preparation of Compound 114

Aqueous 2N sodium hydroxide (0.31 ml) was added to a solution of Compound 25 (65 mg) in methanol (1 ml) and the mixture was stirred at room temperature for 1 hour. The methanol was distilled off under reduced pressure. The residue was extracted by addition of chloroform and water. Sodium bisulfate was added to the aqueous layer to adjust to pH 3 and the mixture was extracted with ethyl acetate. The ethyl acetate layer was washed with saturated saline solution and dried over anhydrous magnesium sulfate. The solvent was distilled off and the residue was crystallized from diethyl ether to obtain 2-(6-carboxy-2,2-dimethyl-2H-1,3-benzoxazine-4-yl)pyridine 1-oxide (46 mg) (Compound 114).

EXAMPLE 36

Preparation of Compound 115

Ethyl chlorocarbonate(80 mg) was added to a solution of Compound 113 (200 mg) and triethylamine (0.10 ml) in anhydrous tetrahydrofuran (1 ml) at −15° C. under an argon atmosphere and the mixture was stirred at −15° to −10° C. for 30 minutes. The resulting precipitate was filtered off and the filtrate was added to a solution of sodium borohydride (67 mg) in water (0.7 ml) at 10° C. After completion of the addition, the mixture was allowed to warm to room temperature and stirred for 3 hours. The mixture was extracted by addition of water and ethyl acetate. The organic layer was washed with saturated saline solution and dried over anhydrous magnesium sulfate. The solvent was distilled off and the residue was purified by silica gel column chromatography to obtain 6-hydroxymethyl-2,2-dimethyl-4-(2-pyridyl)-2H-1,3-benzoxazine (110 mg) (Compound 115). Likewise, Compound 145 was prepared from Compound 114.

EXAMPLE 37

Preparation of Compound 116

Active manganese dioxide (300 mg) was added to a solution of Compound 115 (100 mg) in dichloromethane (3 ml) and the mixture was stirred at room temperature for 1 hour. The insoluble substance was filtered off through celite and the filtrate was distilled off under reduced pressure to obtain 6-formyl-2,2-dimethyl-4-(2-pyridyl)-2H-1,3-benzoxazine (40 mg) (Compound 116). Likewise, Compound 146 was prepared from Compound 145.

EXAMPLE 38

Preparation of Compound 138

According to the same manner as that described in Example 29 for the preparation of Compound 99, 6-trifluoromethyl-4-(3-methoxy-2-pyridyl)-2,2-dimethyl-2H-1,3-benzoxazine (Compound 138) was prepared from 3-methoxypyridine and 2-cyano-4-trifluoromethylphenol except that 1.6M butyllithium in hexane and N,N,N',N'-tetramethylethylenediamine was used instead of 1.6M butyllithium.

Likewise, Compound 139 was prepared from 3-ethoxypyridine.

EXAMPLE 39

Preparation of Compound 140

To a solution of Compound 136 (1.68 g) in dimethylformamide (10 ml) was added cuprous cyanide (0.91 g) and the mixture was heated under reflux in argon atmosphere. The reaction mixture was poured into a mixture of ethylenediamine (5 ml) and water (50 ml) and the resulting mixture was extracted twice with ethyl acetate. The organic layer was washed in turn with water and saline solution and dried over anhydrous magnesium sulfate. The solvent was distilled off. The residue was purified by colum chromatography eluting with ethyl acetate/hexamen to obtain 6-cyano-2,2-dimethyl-4-(3-methyl-2-pyridyl)-2H-1,3-benzoxazine (0.46 g) (Compound 140).

Likewise, Compounds 141 and 142 were prepared from Compound 135.

EXAMPLE 40

Preparation of Compound 143

To a solution of Compound 133 (0.86 g) in tetrahydrofuran (20 ml) was added tetrabutylammonoium bromide trihydrate (1.13 g) and the mixture was heated under reflux for 5 hours. After air-cooling, the solvent was distilled off and the residue was extracted by addition of ethyl acetate and a saturated aqueous potassium bisufate solution. The ethyl acetate layer was dried over anhydrous magnesium sulfate and the solvent was distilled off. The residue was purified by column chromatography eluting with chloroform/methanol and crystallized from isopropyl ether to obtain 2-(6-bromo-2,2-dimethyl-2H-1,3-benzoxadin-4-yl)-3-hydroxypyridine N-oxide (0.40 g) (Compound 143).

TABLE 2

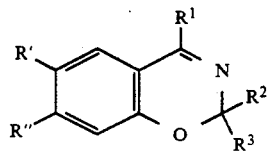

| Comp. No. | R' | R" | R$^1$ | R$^2$ | R$^3$ | Formula | m.p. (°C.) physical property |
|---|---|---|---|---|---|---|---|
| 1 | CN | H | 2-Py | Me | Me | C$_{16}$H$_{13}$N$_3$O | 142–144 |
| 2 | H | H | 2-Py | Me | Me | C$_{15}$H$_{14}$N$_2$O | 78–80 |
| 3 | Me | H | 2-Py | Me | Me | C$_{16}$H$_{16}$N$_2$O | 71–73 |
| 4 | Br | H | 2-Py | Me | Me | C$_{15}$H$_{13}$BrN$_2$O | 94–94.5 |
| 5 | Cl | H | 2-Py | Me | Me | C$_{15}$H$_{13}$ClN$_2$O | 87–87.5 |
| 6 | CO$_2$Me | H | 2-Py | Me | Me | C$_{17}$H$_{16}$N$_2$O$_3$ | 104–106 |
| 7 | Bz | H | 2-Py | Me | Me | C$_{22}$H$_{18}$N$_2$O$_2$ | 176–179 |
| 8 | 4-Cl—Bz | H | 2-Py | Me | Me | C$_{22}$H$_{17}$ClN$_2$O$_2$ | 118–119 |
| 9 | CONH$_2$ | H | 2-Py | Me | Me | C$_{16}$H$_{15}$N$_3$O$_2$ | 214–214.5 |
| 10 | H | Me | 2-Py | Me | Me | C$_{16}$H$_{16}$N$_2$O | 64–66 |
| 11 | NO$_2$ | H | 2-Py | Me | Me | C$_{15}$H$_{13}$N$_3$O$_3$ | 105–108 |
| 12 | CN | H | 3-OH-2-Py | Me | Me | C$_{16}$H$_{13}$N$_3$O$_2$ | 259–262 |
| 13 | CN | H | 2-MeO—Ph | Me | Me | C$_{18}$H$_{16}$N$_2$O$_2$ | 118–119 |
| 14 | CN | H | 2,4,6-triMeO—Ph | Me | Me | C$_{20}$H$_{20}$N$_2$O$_4$ | 200–202 |
| 15 | CN | H | 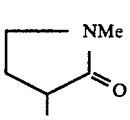 | Me | Me | C$_{16}$H$_{17}$N$_3$O$_2$ | 105–108 |
| 16 | CN | H | 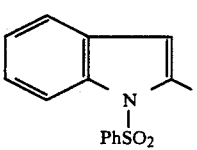 | Me | Me | C$_{25}$H$_{19}$N$_3$O$_3$S | 165–167 |

TABLE 2-continued

| | | | | | | | |
|---|---|---|---|---|---|---|---|
| 17 | CN | H | (cyclohexenyl-Me with NSO₂Ph) | Me | Me | $C_{21}H_{17}N_3O_3S$ | 168–169 |
| 18 | CN | H | (2-methylpyridinium N'-Me, I⁻) | Me | Me | $C_{17}H_{16}IN_3O$ | 205–208 |
| 19 | CN | H | (1-methyl-2-(cyanoimino)imidazolidine) | Me | Me | $C_{15}H_{14}N_6O$ | 235–237 |
| 20 | CN | H | 2-Py–N→O | Me | Me | $C_{16}H_{13}N_3O_2$ | 152–154 |
| 21 | H | H | 2-Py–N→O | Me | Me | $C_{15}H_{14}N_2O_2$ | 163–165 |
| 22 | Me | H | 2-Py–N→O | Me | Me | $C_{16}H_{16}N_2O_2$ | 188–189 |
| 23 | Br | H | 2-Py–N→O | Me | Me | $C_{15}H_{13}BrN_2O_2 \cdot 1.5H_2O$ ($C_{15}H_{13}BrN_2O_2$) | 80–81 (147.5–148.5) |
| 24 | Cl | H | 2-Py–N→O | Me | Me | $C_{15}H_{13}ClN_2O_2$ | 157.5–158.5 |
| 25 | CO₂Me | H | 2-Py–N→O | Me | Me | $C_{17}H_{16}N_2O_4$ | 138–141 |
| 26 | Bz | H | 2-Py–N→O | Me | Me | $C_{22}H_{18}N_2O_3$ | 158–162 |
| 27 | 4-Cl–Bz | H | 2-Py–N→O | Me | Me | $C_{22}H_{17}ClN_2O_3$ | 98–104 |
| 28 | CONH₂ | H | 2-Py–N→O | Me | Me | $C_{16}H_{15}N_3O_3$ | 225–231 |
| 29 | NO₂ | H | 2-Py–N→O | Me | Me | $C_{15}H_{13}N_3O_4$ | 220–221 |
| 30 | CO₂Bu$^t$ | H | 2-Py | Me | Me | $C_{20}H_{22}N_2O_3$ | 106–108 |
| 31 | PhSO₂ | H | 2-Py | Me | Me | $C_{21}H_{18}N_2O_3S$ | 103–104 |
| 32 | PhSO₂ | H | 2-Py–N→O | Me | Me | $C_{21}H_{18}N_2O_4S$ | oily |
| 33 | CN | H | (3-(2-(trimethylsilyl)ethoxymethoxy)-4-SiMe₃-2-methylpyridine) | Me | Me | $C_{26}H_{36}N_3O_3Si_2$ | oily |
| 34 | CN | H | (1-methyl-2-(cyanoimino)thiazolidine) | Me | Me | $C_{15}H_{13}N_5OS$ | 298–300 |
| 35 | SO₂NH₂ | H | 2-Py | Me | Me | $C_{15}H_{15}N_3O_3S$ | 226–228 |
| 36 | SO₂NH₂ | H | 2-Py–N→O | Me | Me | $C_{15}H_{15}N_3O_4S$ | 133–138 |
| 37 | CN | H | 3-EtO-2-Py | Me | Me | $C_{18}H_{17}N_3O_2$ | oily |
| 38 | CN | H | 3-EtO-2-Py–N→O | Me | Me | $C_{18}H_{17}N_3O_3$ | 148–150 |

TABLE 2-continued

| # | | | | | | | |
|---|---|---|---|---|---|---|---|
| 39 | CN | H | 2-MeS—Ph | Me | Me | $C_{18}H_{16}N_2OS$ | 119–121 |
| 40 | CN | H | 2-MeS(O)—Ph | Me | Me | $C_{18}H_{16}N_2O_2S$ | 169–172 |
| 41 | CN | H | (3,4-dihydro-2H-thiopyran-6-yl) | Me | Me | $C_{16}H_{16}N_2O_5$ | oily |
| 42 | CN | H | (3,4-dihydro-2H-thiopyran-6-yl S-oxide) | Me | Me | $C_{16}H_{16}N_2O_2S$ | oily |
| 43 | $CO_2Bu^t$ | H | 2-Py—N→O | Me | Me | $C_{20}H_{22}N_2O_4$ | 120–123 |
| 44 | Bz | Me | 2-Py | Me | Me | $C_{23}H_{20}N_2O_2$ | 169–171 |
| 45 | Bz | Me | 2-Py—N→O | Me | Me | $C_{23}H_{20}N_2O_3$ | 192–195 |
| 46 | Br | Me | 2-Py | Me | Me | $C_{16}H_{15}BrN_2O$ | 119–124 |
| 47 | Br | Me | 2-Py—N→O | Me | Me | $C_{16}H_{15}BrN_2O_2$ | 224–232 |
| 48 | $NO_2$ | Me | 2-Py | Me | Me | $C_{16}H_{15}N_3O_3$ | 139–143 |
| 49 | $NO_2$ | Me | 2-Py—N→O | Me | Me | $C_{16}H_{15}N_3O_4$ | 198–202 |
| 50 | $Me_3SiC{\equiv}C$ | H | 2-Py | Me | Me | $C_{20}H_{22}N_2OSi$ | 88.5–89.5 |
| 51 | $Me_3SiC{\equiv}C$ | H | 2-Py—N→O | Me | Me | $C_{20}H_{22}N_2O_2Si$ | 91–92 |
| 52 | $HC{\equiv}C$ | H | 2-Py | Me | Me | $C_{17}H_{14}N_2O$ | oily |
| 53 | $HC{\equiv}C$ | H | 2-Py—N→O | Me | Me | $C_{17}H_{14}N_2O_2$ | 162–163 |
| 54 | 2-Py | H | 2-Py | Me | Me | $C_{20}H_{17}N_3O$ | oily |
| 55 | Ac | H | 2-Py | Me | Me | $C_{17}H_{16}N_2O_2$ | 97–98 |
| 56 | Ac | H | 2-Py—N→O | Me | Me | $C_{17}H_{16}N_2O_3$ | 117.5–118.5 |
| 57 | Me | 8-$NO_2$ | 2-Py | Me | Me | $C_{16}H_{15}N_3O_3$ | 153–155 |
| 58 | Me | 8-$NO_2$ | 2-Py—N→O | Me | Me | $C_{16}H_{15}N_3O_4$ | 173–176 |
| 59 | Br | 7-Me 8-Br | 2-Py | Me | Me | $C_{16}H_{14}Br_2N_2O$ | |
| 60 | Br | 7-Me 8-Br | 2-Py—N→O | Me | Me | $C_{16}H_{14}Br_2N_2O_2$ | 183–185 |
| 61 | H | EtO | 2-Py | Me | Me | $C_{17}H_{18}N_2O_2$ | oily |
| 62 | Br | EtO | 2-Py | Me | Me | $C_{17}H_{17}BrN_2O_2$ | 111–114 |
| 63 | Br | EtO | 2-Py—N→O | Me | Me | $C_{17}H_{17}BrN_2O_3$ | 129–134 |
| 64 | CN | Me | 2-Py | Me | Me | $C_{17}H_{15}N_3O$ | 145–149 |
| 65 | CN | Me | 2-Py—N→O | Me | Me | $C_{17}H_{15}N_3O_2$ | 186–189 |
| 66 | $NO_2$ | EtO | 2-Py | Me | Me | $C_{17}H_{17}N_3O_4$ | 134–139 |
| 67 | $NO_2$ | EtO | 2-Py—N→O | Me | Me | $C_{17}H_{17}N_3O_5$ | 158–163 |
| 68 | $CF_3O$ | H | 2-Py | Me | Me | $C_{16}H_{13}F_3N_2O_2$ | oily |
| 69 | $CF_3O$ | H | 2-Py—N→O | Me | Me | $C_{16}H_{13}F_3N_2O_3$ | 105–107 |

TABLE 2-continued

| | | | | | | | |
|---|---|---|---|---|---|---|---|
| 70 | MeO | H | 2-Py | Me | Me | $C_{16}H_{16}N_2O_2$ | 68–69 |
| 71 | MeO | H | 2-Py—N→O | Me | Me | $C_{16}H_{15}N_2O_3$ | 148–149 |
| 72 | MeO | 5-$NO_2$ | 2-Py | Me | Me | $C_{16}H_{15}N_3O_4$ | 220.5–222 |
| 73 | MeO | 5-$NO_2$ | 2-Py—N→O | Me | Me | $C_{16}H_{15}N_3O_5$ | 225–230 |
| 74 | $CF_3$ | H | 2-Py | Me | Me | $C_{16}H_{13}F_3N_2O$ | 59–59.5 |
| 75 | $CF_3$ | H | 2-Py—N→O | Me | Me | $C_{16}H_{13}F_3N_2O_2 \cdot 0.5H_2O$ ($C_{16}H_{13}F_3N_2O_2$) | 91.5–92.5 (123–123.5) |
| 76 | $C_2F_5$ | H | 2-Py | Me | Me | $C_{17}H_{13}F_5N_2O$ | oily |
| 77 | $C_2F_5$ | H | 2-Py—N→O | Me | Me | $C_{17}H_{13}F_5N_2O_2$ | 135–137 |
| 78 | Cl | Cl | 2-Py | Me | Me | $C_{15}H_{12}Cl_2N_2O$ | 104–105 |
| 79 | Cl | Cl | 2-Py—N→O | Me | Me | $C_{15}H_{12}Cl_2N_2O_2$ | 156–157 |
| 80 | Et | H | 2-Py | Me | Me | $C_{17}H_{18}N_2O$ | oily |
| 81 | Et | H | 2-Py—N→O | Me | Me | $C_{17}H_{18}N_2O_2$ | 93–95 |
| 82 | —CH=CH—CH=CH— | | 2-Py | Me | Me | $C_{19}H_{16}N_2O$ | 82–85 |
| 83 | —CH=CH—CH=CH— | | 2-Py—N→O | Me | Me | $C_{19}H_{16}N_2O_2$ | 136–140 |
| 84 | H | Cl | 2-Py | Me | Me | $C_{15}H_{13}ClN_2O$ | 81–83 |
| 85 | H | Cl | 2-Py—N→O | Me | Me | $C_{15}H_{13}ClH_2O_2$ | 134–137 |
| 86 | CN | EtO | 2-Py | Me | Me | $C_{18}H_{17}N_3O_2$ | 142–148 |
| 87 | CN | EtO | 2-Py—N→O | Me | Me | $C_{18}H_{17}N_3O_3$ | 184–186 |
| 88 | Br | Cl | 2-Py | Me | Me | $C_{15}H_{12}BrClN_2O$ | 100–103 |
| 89 | Br | Cl | 2-Py—N→O | Me | Me | $C_{15}H_{12}BrClN_2O_2$ | 184–186 |
| 90 | CN | Cl | 2-Py | Me | Me | $C_{16}H_{12}ClN_3O$ | 129–132 |
| 91 | CN | Cl | 2-Py—N→O | Me | Me | $C_{16}H_{12}ClN_3O_2$ | 232–244 (decomp.) |
| 92 | Br | Br | 2-Py | Me | Me | $C_{15}H_{12}Br_2N_2O$ | 99–101 |
| 93 | Br | Br | 2-Py—N→O | Me | Me | $C_{15}H_{12}Br_2N_2O_2$ | 199–202 |
| 94 | Br | F | 2-Py | Me | Me | $C_{15}H_{12}BrFN_2O$ | 119–121 |
| 95 | Br | F | 2-Py—N→O | Me | Me | $C_{15}H_{12}BrFN_2O_2$ | 186–187 |
| 96 | CN | H | 3-Py | Me | Me | $C_{16}H_{13}N_3O$ | 123–126 |
| 97 | CN | H | 3-Py—N→O | Me | Me | $C_{16}H_{13}N_3O_2$ | 181–182.5 |
| 98 | Br | H | 3-Py | Me | Me | $C_{15}H_{13}BrN_2O$ | oily |
| 99 | Br | H | 4-Py | Me | Me | $C_{15}H_{13}BrN_2O$ | 89–91 |
| 100 | Br | H | 4-Me-2-Py | Me | Me | $C_{16}H_{15}BrN_2O$ | 81–85 |
| 101 | Br | H | 2-BnO—Ph | Me | Me | $C_{29}H_{20}BrNO_2$ | 124–127 |
| 102 | Br | H | 1-isoquinolyl | Me | Me | $C_{19}H_{16}BrN_2O$ | 157–160 |
| 103 | Br | H | 2-quinolyl | Me | Me | $C_{19}H_{15}BrN_2O$ | oily |

TABLE 2-continued

| | | | | | | | |
|---|---|---|---|---|---|---|---|
| 104 | Br | H | (structure: 4-bromo-2-(substituted)phenol with HO, attached to a pyrimidine-like ring with two N and Me) | Me | Me | $C_{20}H_{15}BrN_3O_2$ | 199-202 |
| 105 | Br | H | 1,3-dithian-2-yl | Me | Mr | $C_{14}H_{16}BrNOS_2$ | 108-109 |
| 106 | Br | H | 3-Py—N→O | — | Me | $C_{15}H_{19}BrN_2O_2$ | 131.5-133 |
| 107 | Br | H | 4-Py—N→O | Me | Me | $C_{15}H_{19}BrN_2O_2$ | 158-161 |
| 108 | Br | H | 4-Me-2-Py—N→O | Me | Me | $C_{16}H_{15}BrN_2O_2$ | 110-112 |
| 109 | Br | H | 1-isoquinolyl-N→O | Me | Me | $C_{19}H_{19}BrN_2O_2$ | 240-247 (decomp.) |
| 110 | Br | H | 2-quinolyl-N→O | Me | Me | $C_{19}H_{15}BrN_2O_2$ | 135-137 |
| 111 | Br | H | 1,3-dithian-2-yl-N→O | Me | Me | $C_{14}H_{16}BrNO_2S_2$ | 189.5-191 |
| 112 | CON(Boc)$_2$ | H | 2-Py | Me | Me | $C_{26}H_{31}N_3O_6$ | oily |
| 113 | CO$_2$H | H | 2-Py | Me | Me | $C_{16}H_{14}N_2O_3$ | 169-172 |
| 114 | CO$_2$H | H | 2-Py—N→O | Me | Me | $C_{16}H_{14}N_2O_4$ | 245-257 (decomp.) |
| 115 | CH$_2$OH | H | 2-Py | Me | Me | $C_{16}H_{16}N_2O_2$ | oily |
| 116 | CHO | H | 2-Py | Me | Me | $C_{16}H_{14}N_2O_2$ | oily |
| 117 | Br | Cl | 3-EtO-2-Py—N—O | Me | Me | $C_{17}H_{16}BrClN_2O_3$ | 186-188 |
| 118 | CF$_3$ | H | 3-MeO-2-Py—N—O | Me | Me | $C_{17}H_{15}F_3N_2O_3$ | 170-172 |
| 119 | Br | H | 3-EtO-2-Py—N—O | Me | Me | $C_{17}H_{17}BrN_2O_3$ | 124-127 |
| 120 | Br | H | 3-EtO-2-Py | Me | Me | $C_{17}H_{17}BrN_2O_2$ | oily |
| 121 | Br | Cl | 3-EtO-2-Py | Me | Me | $C_{17}H_{16}BrClN_2O_2$ | 85-89 |
| 122 | CN | H | 3-MeO-2-Py | Me | Me | $C_{17}H_{15}N_3O_2$ | oily |
| 123 | Br | Cl | 3-MeO-2-Py | Me | Me | $C_{16}H_{14}BrClN_2O_2$ | 114-118 |
| 124 | CF$_3$ | H | 3-EtO-2-Py—N—O | Me | Me | $C_{18}H_{17}F_3N_2O_3$ | 143-146 |
| 125 | CN | H | 3-MeO-2-Py—N—O | Me | Me | $C_{17}H_{15}N_3O_3$ | 210-225 (dec.) |
| 126 | Br | Cl | 3-MeO-2-Py—N—O | Me | Me | $C_{16}H_{14}BrClN_2O_3$ | 172-175 |
| 127 | Br | H | 3-Me-2-Py—N—O | Me | Me | $C_{16}H_{15}BrN_2O_2$ | 193-198 |
| 128 | CN | H | 3-Me-2-Py—N—O | Me | Me | $C_{17}H_{15}N_3O_2$ | 185-189 |
| 129 | Br | H | 3-MeO-2-Py—N—O | Me | Me | $C_{16}H_{15}BrN_2O_3$ | 207-210 |
| 130 | Br | H | 3-Cl-2-Py—N—O | Me | Me | $C_{15}H_{12}BrClN_2O_2$ | 217-220 |
| 131 | Br | H | 3-CN-2-Py—N—O | Me | Me | $C_{16}H_{12}BrN_3O_2$ | amorphous |
| 132 | CN | H | 3-CN-2-Py—N—O | Me | Me | $C_{17}H_{12}N_4O_2$ | amorphous |
| 133 | Br | H | (structure: pyridine N-oxide with 2-methyl and 3-OCH$_2$OCH$_2$CH$_2$SiMe$_3$) | Me | Me | $C_{21}H_{27}BrN_2O_4Si$ | oily |
| 134 | Br | H | 3-MeO-2-Py | Me | Me | $C_{16}H_{15}BrN_2O_2$ | oily |
| 135 | Br | H | 3-Cl-2-Py | Me | Me | $C_{15}H_{12}BrClN_2O$ | oily |
| 136 | Br | H | 3-Me-2-Py | Me | Me | $C_{16}H_{15}BrN_2O$ | oily |
| 137 | Br | H | (structure: pyridine with 2-methyl and 3-OCH$_2$OCH$_2$CH$_2$SiMe$_3$) | Me | Me | $C_{21}H_{27}BrN_2O_3Si$ | oily |
| 138 | CF$_3$ | H | 3-MeO-2-Py | Me | Me | $C_{17}H_{15}F_3N_2O_2$ | oily |
| 139 | CF$_3$ | H | 3-EtO-2-Py | Me | Me | $C_{18}H_{17}F_3N_2O_2$ | oily |
| 140 | CN | H | 3-Me-2-Py | Me | Me | $C_{17}H_{15}N_3O$ | oily |
| 141 | Br | H | 3-CN-2-Py | Me | Me | $C_{16}H_{12}BrN_3$ | 115-117 |
| 142 | CN | H | 3-CN-2-Py | Me | Me | $C_{17}H_{12}N_4O$ | 155-157 |
| 143 | Br | H | 3-OH-2-Py—N—O | Me | Me | $C_{15}H_{13}BrN_2O_3$ | 155-159 |

TABLE 2-continued

| | | | | | | | |
|---|---|---|---|---|---|---|---|
| 144 | CON(Boc)$_2$ | H | 2-Py—N→O | Me | Me | C$_{26}$H$_{31}$N$_3$O$_7$ | 117–121 |
| 145 | CH$_2$OH | H | 2-Py—N→O | Me | Me | C$_{16}$H$_{16}$N$_2$O$_3$ | 184–187 |
| 146 | CHO | H | 2-Py—N→O | Me | Me | C$_{16}$H$_{14}$N$_2$O$_3$ | 179–181 |

Py: Pyridyl, 2-Py—N→O: 2-Pyridyl N-Oxide,
Bz: Benzoyl
Bn: Benzyl,
Boc: t-Butyloxycarbonyl

| Comp. No. | NMR TMS internal standard (ppm), CDCl$_3$ | IR KBr (cm$^{-1}$) |
|---|---|---|
| 1 | 1.71(6H, s), 6.94(1H, d), 7.41–7.48(1H, m), 7.62(1H, dd) 7.85–7.88(2H, m), 8.25(1H, d), 8.7–8.8(1H, m) | 3070, 3000, 2230, 1620, 1565, 1340, 1270, 1120 |
| 2 | 1.69(6H, s), 6.87–6.95(2H, m), 7.32–7.42(2H, m), 7.57(1H, dd), 7.75–7.87(2H, m), 8.69–8.72(1H, m) | 2980, 1620, 1600, 1570, 1340, 1260, 1150, 1115 |
| 3 | 1.67(6H, s), 2.25(3H, s), 6.79(1H, d), 7.14–7.20(1H, m), 7.31–7.42(2H, m), 7.72–7.87(2H, m), 8.70–8.74(1H, m) | 3000, 1615, 1565, 1365, 1335, 1265, 1200, 1141 |
| 4 | 1.67(6H, s), 6.78(1H, d), 7.35–7.50(2H, m), 7.75–7.90 (3H, m), 8.72(1H, dt) | |
| 5 | 1.67(6H, s), 6.83(1H, d), 7.31(1H, dd), 7.41(1H, m), 7.7(1H, d), 7.76–7.90(2H, m), 8.71(1H, dt) | |
| 6 | 1.70(6H, s), 3.86(3H, s), 6.92(1H, d), 7.42(1H, m), 7.76–7.90(2H, m), 8.06(1H, dd), 8.34(1H, d), 8.71–8.76(1H, m) | |
| 7 | 1.72(6H, s), 6.96(1H, d), 7.33–7.63(4H, m), 7.78–7.86 (4H, m), 7.89(1H, dd), 8.26(1H, d), 8.64(1H, m) | |
| 8 | 1.72(6H, s), 6.97(1H, d), 7.35–7.50(3H, m), 7.73–7.90 (5H, m), 8.26(1H, d), 8.62–8.67(1H, m) | |
| 9 | 1.70(6H, s), 5.50–6.10(2H, bs), 6.94(1H, d), 7.42(1H, td), 7.80–7.90(3H, m), 8.21(1H, d), 8.71(1H, dt) | |
| 10 | 1.67(6H, s), 2.33(3H, s), 6.71(1H, bs), 6.72(1H, d), 7.36 (1H, m), 7.42(1H, m), 7.71–7.87(2H, m), 8.70(1H, m) | |
| 11 | 1.73(6H, s), 6.97(1H, d), 7.42–7.49(1H, m), 7.81–7.92 (2H, m), 8.26(1H, dd), 8.72–8.75(1H, m), 8.83(1H, d) | 2980, 1610, 1520, 1460, 1340, 1320, 1280, 1260 |
| 12 | 1.85(6H, s), 7.15(1H, d), 7.20–7.60(1H, bs), 7.51–7.81 (4H, m), 8.48(1H, d) | 2990, 2220, 1620, 1590, 1550, 1490, 1300, 1230 |
| 13 | 1.71(6H, s), 3.75(3H, s), 6.90(1H, d), 7.00(1H, d), 7.03–7.11(1H, m), 7.18(1H, d), 7.27–7.31(1H, m), 7.42–7.51 (1H, m), 7.56(1H, dd) | 2980, 2230, 1630, 1605, 1480, 1455, 1300, 1290, 1275, 760 |
| 14 | 1.71(6H, s), 3.72(6H, s), 3.87(3H, s), 6.19(2H, s), 6.86(1H, d), 7.12(1H, d), 7.53(1H, dd) | 2980, 2230, 1635, 1610, 1590, 1485, 1330, 1230 |
| 15 | 1.57(6H, s), 2.20–2.38(1H, m), 2.65–2.81(1H, m), 2.90 (3H, s), 3.40–3.67(2H, m), 4.45(1H, dd), 7.06(1H, d), 7.72 (1H, dd), 8.42(1H, d) | 2990, 2220, 1690, 1640, 1490, 1360, 1300, 1210, 1180 |
| 16 | 1.79(6H, s), 6.86(1H, s), 6.95(1H, d), 7.30–7.63(8H, m), 7.83–7.87(2H, m), 8.14–8.18(1H, m) | 2990, 2220, 1640, 1490, 1450, 1370, 1290, 1180 |
| 17 | 1.65(6H, s), 6.40–6.47(2H, m), 6.90(1H, d), 7.24–7.28 (1H, m), 7.44–7.61(5H, m), 7.81–7.85(2H, m) | 2980, 2220, 1640, 1490, 1370, 1290, 1180, 1150 |
| 18 | 1.75(6H, s), 4.52(3H, s), 7.03(1H, d), 7.71–7.79(2H, m), 8.02(1H, d), 8.30–8.37(1H, m), 8.71–8.80(1H, m), 9.75 (1H, d) | 3000, 2220, 1640, 1620, 1490, 1290, 1125, 870 |
| 19 | 1.56(6H, s), 3.74(2H, t), 4.06(2H, t), 6.91(1H, d), 7.60 (1H, dd), 7.70(1H, d), 7.60–7.82(1H, bs) | 2980, 2230, 2190, 1630, 1495, 1370, 1280 |
| 20 | 1.73(6H, s), 6.93(1H, d), 7.25–7.27(1H, m), 7.38–7.50 (3H, m), 7.58(1H, dd), 8.29–8.32(1H, m) | 2980, 2230, 1650, 1610, 1480, 1430, 1280, 1230 |
| 21 | 1.71(6H, s), 6.82–6.98(3H, m), 7.29–7.48(4H, m), 8.26–8.30(1H, m) | 2970, 1622, 1488, 1455, 1430, 1385, 1365, 1260 |
| 22 | 1.69(6H, s), 2.19(3H, s), 6.72–6.78(2H, m), 7.12–7.17 (1H, m), 7.34–7.43(3H, m), 8.27–8.31(1H, m) | 2980, 1630, 1430, 1270, 1250, 1150, 1120 |
| 23 | 1.70(6H, s), 6.76(1H, d), 7.04(1H, d), 7.30–7.50(4H, m), 8.25–8.35(1H, m) | |
| 24 | 1.70(6H, s), 6.81(1H, d), 6.92(1H, d), 7.20–7.50(4H, m), 8.29(1H, dd) | |
| 25 | 1.72(6H, s), 3.81(3H, s), 6.90(1H, d), 7.36–7.52(3H, m), 7.59(1H, d), 8.02(1H, dd), 8.27–8.34(1H, m) | |
| 26 | 1.75(6H, s), 6.93(1H, d), 7.32–7.60(7H, m), 7.73–7.87 (3H, m), 8.21–8.27(1H, m) | |
| 27 | 1.74(6H, s), 6.94(1H, d), 7.34–7.50(6H, m), 7.70–7.78 (2H, m), 7.80(1H, dd), 8.21–8.26(1H, m) | |
| 28 | 1.72(6H, s), 5.20–6.50(2H, bs), 6.90(1H, d), 7.38–7.52 (4H, m), 7.80(1H, dd), 8.29(1H, dd) | |
| 29 | 1.75(6H, s), 6.95(1H, d), 7.36–7.52(3H, m), 7.83(1H, d), 8.20–8.33(2H, m) | 2980, 1640, 1620, 1520, 1440, 1340, 1325, 1255 |
| 30 | 0.99(6H, d), 1.70(6H, s), 2.03(1H, m), 4.05(2H, d), 6.92 (1H, d), 7.41(1H, m), 7.78–7.90(2H, m), 8.06(1H, dd), 8.42(1H, d), 8.68–8.74(1H, m) | |
| 31 | 1.68(6H, s), 6.95(1H, d), 7.40–7.60(4H, m), 7.70–8.10 (5H, m), 8.44(1H, d), 8.69(1H, m) | |
| 32 | 1.70(6H, s), 6.92(1H, d), 7.40–7.65(7H, m), 7.70–7.90 | |

TABLE 2-continued

| | | |
|---|---|---|
| | (3H, m), 8.30-8.36(1H, m) | |
| 33 | -0.05(9H, s), 0.35(9H, s), 0.70(2H, t), 1.73(6H, s), 3.50 (2H, t), 5.05(2H, s), 6.91(1H, d), 7.15-7.67(3H, m), 8.45 (1H, d) | |
| 34 | 1.61(6H, s), 3.57(2H, t), 4.28(2H, t), 6.94(1H, d), 7.51(1H, d), 7.63 (1H, dd) | 2230, 2180, 1650, 1560, 1340, 1280, 1200, 1120 |
| 35 | *1.69(6H, s), 6.41(2H, s), 6.96(1H, d), 7.38-7.48(1H, m), 7.79-7.97 (3H, m), 8.32(1H, d), 8.70(1H, d) | 3300, 3160, 3060, 1615, 1560, 1460, 1370, 1265 |
| 36 | 1.72(6H, s), 6.94(1H, d), 7.41-7.58(4H, m), 7.87(1H, dd), 8.22-8.31 (1H, m) | 3420, 1635, 1480, 1430, 1340, 1230, 1155, 1120 |
| 37 | 1.28(3H, t), 1.74(6H, s), 4.05(2H, q), 6.92(1H, d), 7.19(1H, d), 7.35-7.38(2H, m), 7.55-7.60(2H, m), 8.32(1H, d) | |
| 38 | 1.34(3H, t), 1.71&1.79(6H, s), 4.10-4.15(2H, m), 6.89-6.99(2H, m), 7.04-7.15(1H, m), 7.30-7.36(1H, m), 7.58(1H, dd), 7.96-8.00(1H, m) | 3430, 2980, 2230, 1635, 1485, 1430, 1300, 1280, 1235, 1110, 1090 |
| 39 | 1.74(6H, s), 2.43(3H, s), 6.92(1H, d), 7.14-7.50(5H, m), 7.58(1H, dd) | 2225, 1640, 1485, 1310, 1290, 1275, 1115, 980 |
| 40 | 1.64&1.76(6H, s), 2.92(3H, s), 6.99(1H, d), 7.40-7.45(2H, m), 7.58-7.70 (2H, m), 7.75-7.83(1H, m), 8.30-8.35(1H, m) | 2225, 1620, 1340, 1280, 1120, 1065, 1035, 865 |
| 41 | 1.61(6H, s), 2.01-2.14(2H, m), 2.28-2.42(2H, m), 2.95-3.06(2H, m), 6.05(1H, t), 6.89(1H, d), 7.59(1H, dd), 7.82(1H, d) | |
| 42 | 1.59&1.74(6H, s), 1.90-2.12(2H, m), 2.28-2.58(2H, m), 2.71-3.00& 3.10-3.35(2H, m), 6.60-6.66(1H, m), 6.93(1H, d), 7.63(1H, dd), 7.70 (1H, d) | 2990, 2935, 2230, 1725, 1620, 1480, 1330, 1230, 1120 |
| 43 | 0.95(6H, d), 1.72(6H, s), 1.99(1H, m), 4.01(2H, d), 6.90(1H, d), 7.32-7.50 (3H, m), 7.61(1H, d), 8.02(1H, dd), 8.25-8.31(1H, m) | |
| 44 | 1.71(6H, s), 2.41(3H, s), 6.83(1H, s), 7.26-7.36(1H, m), 7.41-7.63 (3H, m), 7.70-7.90(5H, m), 8.51-8.56(1H, m) | |
| 45 | 1.73(6H, s), 2.34(3H, s), 6.79(1H, s), 6.99(1H, s), 7.23-7.62(5H, m), 7.79-7.88(2H, m), 8.11-8.17(1H, m) | |
| 46 | 1.66(6H, s), 2.37(3H, s), 6.79(1H, s), 7.39(1H, m), 7.76-7.89(3H, m), 8.68-8.74(1H, m) | |
| 47 | 1.68(6H, s), 2.34(3H, s), 6.77(1H, s), 7.06(1H, s), 7.30-7.48(3H, m), 8.24-8.32(1H, m) | |
| 48 | 1.71(6H, s), 2.64(3H, s), 6.80(1H, s), 7.44(1H, m), 7.80-7.93(2H, m), 8.69(1H, s), 8.70-8.75(1H, m) | |
| 49 | 1.73(6H, s), 2.62(3H, s), 6.78(1H, s), 7.34-7.52(3H, m), 7.71(1H, s), 8.26-8.32(1H, m) | |
| 50 | 0.21(9H, s), 1.67(6H, s), 6.82(1H, d), 7.25-7.50(2H, m), 7.70-7.90 (3H, m), 8.74(1H, m) | |
| 51 | 0.19(9H, s), 1.70(6H, s), 6.80(1H, d), 7.04(1H, d), 7.30-7.80(4H, m), 8.30(1H, m) | |
| 52 | 1.69(6H, s), 2.96(1H, s), 6.84(1H, d), 7.35-7.55(2H, m), 7.70-7.90 (3H, m), 8.73(1H, m) | |
| 53 | 1.71(6H, s), 2.93(1H, s), 6.82(1H, d), 7.07(1H, d), 7.35-7.50(4H, m), 8.28(1H, m) | |
| 54 | 1.71(6H, s), 7.00(1H, d), 7.17(1H, m), 7.35(1H, m), 7.55-7.75(2H, m), 7.80-7.90(2H, m), 8.02(1H, dd), 8.21(1H, d), 8.60(1H, m), 8.73(1H, m) | EI-MS; m/z 315(M$^+$) |
| 55 | 1.71(6H, s), 2.52(3H, s), 6.93(1H, d), 7.43(1H, m), 7.80-7.94(2H, m), 8.01(1H, dd), 8.37(1H, d), 8.73(1H, dt) | |
| 56 | 1.73(6H, s), 2.47(3H, s), 6.92(1H, d), 7.35-7.50(3H, m), 7.55(1H, d), 7.95(1H, dd), 8.29(1H, m) | |
| 57 | 1.73(6H, s), 2.33(3H, s), 7.40-7.47(1H, m), 7.77-7.95(4H, m), 8.68-8.73 (1H, m) | 1630, 1610, 1575, 1530, 1335, 1285, 1275, 1130 |
| 58 | 1.76(6H, s), 2.27(3H, s), 6.85-6.95(1H, m), 7.38-7.52(3H, m), 7.77-7.83 (1H, m), 8.25-8.31(1H, m) | 1635, 1575, 1530, 1425, 1360, 1340, 1280, 1255 |
| 59 | 1.71(6H, s), 2.60(3H, s), 7.40(1H, m), 7.77-7.86(2H, m), 7.91(1H, s), 8.68-8.73(1H, m) | |
| 60 | 1.73(6H, s), 2.57(3H, s), 7.08(1H, s), 7.32-7.47(3H, m), 8.25-8.31 (1H, m) | |
| 61 | 1.42(3H, t), 1.68(6H, s), 4.05(2H, q), 6.39-6.49(2H, m), 7.32-7.42 (1H, m), 7.51(1H, d), 7.72-7.87(2H, m), 8.67-8.73(1H, m) | EI-MS; m/z 282(M$^+$) |
| 62 | 1.48(3H, t), 1.67(6H, s), 4.11(2H, q), 6.42(1H, s), 7.38(1H, m), 7.72-7.87(2H, m), 7.89(1H, s), 8.67-8.73(1H, m) | |
| 63 | 1.47(3H, t), 1.65(6H, s), 4.06(2H, q), 6.63(1H, s), 7.23-7.36(2H, m), 7.41(1H, s), 7.47-7.55(1H, m), 8.20-8.26(1H, m) | |
| 64 | 1.69(6H, s), 2.52(3H, s), 6.80(1H, s), 7.38-7.49(1H, m), 7.82-7.88 (2H, m), 8.17(1H, s), 8.68-8.74(1H, m) | |
| 65 | 1.71(6H, s), 2.49(3H, s), 6.78(1H, s), 7.19(1H, s), 7.32-7.48(3H, m), 8.25-8.32(1H, m) | |
| 66 | 1.51(3H, t), 1.70(6H, s), 4.20(2H, q), 6.49(1H, s), 7.38-7.47(1H, m), 7.79-7.90(2H, m), 8.62(1H, s), 8.68-8.75(1H, m) | |
| 67 | 1.50(3H, t), 1.73(6H, s), 4.19(2H, q), 6.47(1H, s), 7.33-7.50(3H, m), 7.63(1H, s), 8.26-8.32(1H, m) | |
| 68 | 1.68(6H, s), 6.88(1H, d), 7.19-7.26(1H, m), 7.34-7.46(1H, m), 7.69 (1H, d), 7.82-7.85(2H, m), 8.68-8.72(1H, m) | |
| 69 | 1.71(6H, s), 6.81(1H, d), 6.87(1H, d), 7.17-7.23(1H, m), 7.30-7.48 (2H, m), 8.26-8.30(1H, m) | 3070, 1625, 1485, 1435, 1280, 1255, 1170, 1145 |
| 70 | 1.66(6H, s), 3.73(3H, s), 6.83(1H, d), 6.96(1H, dd), 7.20(1H, d), 7.38(1H, m), 7.7-7.9(2H, m), 8.70(1H, m) | |
| 71 | 1.69(6H, s), 3.68(3H, s), 6.49(1H, d), 6.81(1H, d), 6.93(1H, dd), 7.3-7.5(3H, m), 8.27(1H, m) | |

TABLE 2-continued

| | | |
|---|---|---|
| 72 | 1.68(6H, s), 3.90(3H, s), 7.13&7.19(2H, ABq), 7.32(1H, td), 7.78 (2H, m), 8.45(1H, m) | |
| 73 | 1.56(3H, s), 1.82(3H, s), 3.83(3H, s), 7.08&7.13(2H, ABq), 7.3–7.4 (3H, m), 8.09(1H, m) | |
| 74 | 1.70(6H, s), 6.96(1H, d), 7.42(1H, m), 7.60(1H, m), 7.8–7.9(2H, m), 8.05(1H, d), 8.71(1H, m) | |
| 75 | 1.72(6H, s), 6.94(1H, d), 7.17(1H, d), 7.3–7.5(3H, m), 7.57(1H, m), 8.29(1H, m) | |
| 76 | 1.71(6H, s), 6.98(1H, d), 7.42(1H, m), 7.57(1H, m), 7.8–7.9(2H, m), 8.05(1H, d), 8.71(1H, m) | |
| 77 | 1.73(6H, s), 6.96(1H, d), 7.13(1H, d), 7.3–7.5(3H, m), 7.53(1H, dd), 8.29(1H, m) | |
| 78 | 1.69(6H, s), 7.01(1H, s), 7.35–7.47(1H, m), 7.82–7.86(2H, m), 7.94 (1H, s), 8.68–8.72(1H, m) | 2990, 1610, 1595, 1435, 1365, 1265, 1200, 1115 |
| 79 | 1.69(6H, s), 6.99(1H, s), 7.02(1H, s), 7.35–7.47(3H, m), 8.25–8.30 (1H, m) | 2990, 1630, 1600, 1430, 1280, 1260, 995 |
| 81 | 1.21(3H, t), 1.64(6H, s), 2.60(2H, q), 6.86–7.04(3H, m), 7.26–7.35(2H, m), 7.50–7.56(1H, m), 8.21–8.26(1H, m). | 2970, 1700, 1590, 1515, 1435, 1315, 1280, 1245, 1165 |
| 82 | 1.72(6H, s), 7.26(1H, s), 7.26–7.52(3H, m), 7.64–7.79 (2H, m), 7.80–7.94(2H, m), 8.12(1H, s), 8.76–8.81(1H, m). | |
| 83 | 1.74(6H, s), 7.23(1H, s), 7.23–7.54(6H, m), 7.61–7.70 (2H, m), 8.29–8.36(1H, m). | |
| 84 | 1.68(6H, s), 6.86–6.94(2H, m), 7.39(1H, m), 7.63(1H, m), 7.76–7.89(2H, m), 8.66–8.72(1H, m). | |
| 85 | 1.70(6H, s), 6.79–6.93(3H, m), 7.33–7.49(3H, m), 8.24–8.30(1H, m). | |
| 86 | 1.50(3H, t), 1.69(6H, s), 4.16(2H, q), 6.41(1H, s), 7.36–7.46 (1H, m), 7.80–7.87(2H, m), 8.15(1H, s), 8.66–8.73(1H, m). | |
| 87 | 1.48(3H, t), 1.71(6H, s), 4.14(2H, q), 6.39(1H, s), 7.17(1H, s), 7.35–7.50(3H, m), 8.28–8.35(1H, m). | |
| 88 | 1.67(6H, s), 7.02(1H, s), 7.37–7.45(1H, m), 7.80–7.87(2H, m), 8.07(1H, s), 8.68–8.73(1H, m). | |
| 89 | 1.69(6H, s), 7.01(1H, s), 7.16(1H, s), 7.32–7.48(3H, m), 8.25–8.31(1H, m). | 2990, 1620, 1600, 1250, 1110 |
| 90 | 1.70(6H, s), 7.01(1H, s), 7.45(1H, m), 7.80–7.95(2H, m), 8.42(1H, s), 8.68–8.74(1H, m). | |
| 91 | 1.73(6H, s), 6.99(1H, s), 7.34–7.52(4H, m), 8.25–8.33(1H, m). | |
| 92 | 1.67(6H, s), 7.20(1H, s), 7.37–7.47(1H, m), 7.80–7.88(2H, m), 8.07(1H, s), 8.68–8.74(1H, m). | |
| 93 | 1.69(6H, s), 7.16(1H, s), 7.19(1H, s), 7.32–7.48(3H, m), 8.25–8.32(1H, m). | |
| 94 | 1.67(6H, s), 6.68(1H, d), 7.37–7.45(1H, m), 7.79–7.90(2H, m), 8.03(1H, d), 8.68–8.73(1H, m). | |
| 95 | 1.70(6H, s), 6.67(1H, d), 7.14(1H, d), 7.36–7.47(3H, m), 8.26–8.31(1H, m). | 3050, 2980, 1630, 1610, 1430, 1340, 1300, 1250, 1185, 1120 |
| 96 | 1.70(6H, s), 7.01(1H, d), 7.4–7.5(2H, m), 7.67(1H, dd), 7.86 (1H, dt), 8.7–8.8(2H, m). | 2240, 1620, 1310 |
| 97 | 1.68(6H, s), 7.01(1H, d), 7.35–7.45(2H, m), 7.47(1H, d), 7.69(1H, dd), 8.33(1H, m), 8.42(1H, m). | 3450, 2240, 1630, 1260 |
| 98 | 1.66(6H, s), 6.83(1H, d), 7.24(1H, d), 7.42(1H, m), 7.49 (1H, dd), 7.88(1H, dt), 8.74(1H, dd), 8.80(1H, dd) | |
| 99 | 1.66(6H, s), 6.83(1H, d), 7.22(1H, d), 7.46(2H, dd), 7.50 (1H, dd), 8.77(2H, dd) | |
| 100 | 1.67(6H, s), 2.43(3H, s), 6.78(1H, d), 7.22(1H, m), 7.44 (1H, dd), 7.61(1H, br.s), 7.80(1H, d), 8.56(1H, d) | |
| 101 | 1.65(6H, s), 5.04(2H, s), 6.74(1H, d), 6.98–7.44(11H, m) | |
| 102 | 1.80(6H, s), 6.82(1H, d), 7.08(1H, d), 7.44(1H, dd), 7.59 (1H, m), 7.73(1H, m), 7.78(1H, d), 7.91(1H, d), 8.13(1H, d), 8.64(1H, d) | |
| 103 | 1.71(6H, s), 6.80(1H, d), 7.47(1H, dd), 7.62(1H, m), 7.79 (1H, m), 7.88(1H, d), 7.96(1H, d), 8.19(1H, d), 8.21(1H, d), 8.29(1H, d) | |
| 104 | 1.72(6H, s), 6.83(1H, d), 6.97(1H, d), 7.50(2H, dd), 7.86 (1H, d), 7.95(1H, d), 7.96(1H, d), 8.99(1H, d) | |
| 105 | 1.59(6H, s), 1.90–2.30(2H, m), 2.90–3.10(4H, m), 5.17 (1H, s), 6.70(1H, d), 7.41(1H, dd), 7.71(1H, d) | |
| 106 | 1.64(6H, s), 6.84(1H, d), 7.25(1H, d), 7.35–7.55(2H, m), 7.52(1H, dd), 8.31(1H, dt), 8.43(1H, br.s) | 1620, 1590, 1260, 1240 |
| 107 | 1.63(6H, s), 6.85(1H, d), 7.27(1H, d), 7.48–7.56(3H, m), 8.28(2H, m) | 1610, 1460, 1330, 1260 |
| 108 | 1.70(3H, s), 2.40(3H, s), 6.76(1H, d), 7.07(1H, d), 7.15–7.25 (2H, m), 7.42(1H, dd), 8.18(1H, d) | 1630, 1470, 1270, 1260, 1240 |
| 109 | 1.79(3H, s), 1.83(3H, s), 6.83(1H, d), 6.88(1H, d), 7.44 (1H, dd), 7.56–7.74(3H, m), 7.78(1H, d), 7.80–7.90(1H, m), 8.22(1H, d) | 1620, 1330, 1220 |
| 110 | 1.73(6H, s), 6.79(1H, d), 7.00(1H, d), 7.42(2H, d&dd), 7.71(1H, m), 7.83(2H, m), 7.94(1H, dd), 8.77(1H, d) | |
| 111 | 1.62(3H, s), 1.63(3H, s), 2.16–2.40(1H, m), 2.48–2.72 (1H, m), 2.64–2.82(2H, m), 2.87(1H, m), 3.62(1H, m), 4.77 (1H, s), 6.73(1H, d), 7.45(1H, dd), 7.61(1H, d) | |
| 112 | 1.39(18H, s), 1.71(6H, s), 6.94(1H, d), 7.41(1H, m), 7.78–7.90 (3H, m), 8.37(1H, d), 8.70(1H, m) | |

TABLE 2-continued

| | | |
|---|---|---|
| 113 | 1.71(6H, s), 6.92(1H, d), 7.42(1H, m), 7.76-7.90(2H, m), 8.07(1H, dd), 8.36(1H, d), 8.74(1H, m) | 1700, 1620, 1220 |
| 114 | 1.71(6H, s), 6.85(1H, d), 7.41-7.60(4H, m), 7.95(1H, dd), 8.46(1H, d) | 1700, 1630, 1600, 1200 |
| 115 | 1.68(6H, s), 4.58(2H, s), 6.89(1H, d), 7.36-7.43(2H, m), 7.59(1H, d), 7.76-7.88(2H, m), 8.69(1H, m) | EI-MS 268(M$^+$) |
| 116 | 1.72(6H, s), 7.00(1H, d), 7.39-7.46(1H, m), 7.81-7.94 (3H, m), 8.28(1H, d), 8.72(1H, m), 9.84(1H, s) | 1700, 1620, 1660 (neat) |
| 117 | 1.39(3H, t), 1.67(3H, s), 1.75(3H, s), 4.07(2H, q), 6.93 (1H, d), 7.00(2H, s), 7.27(1H, dd), 7.96(1H, dd) | 1630, 1590, 1420, 1220, 1100 |
| 118 | 1.73(3H, s), 1.77(3H, s), 3.85(3H, s), 6.94(1H, d), 6.96 (1H, d), 7.02(1H, d), 7.31(1H, dd), 7.56(1H, m), 8.00(1H, d) | 1630, 1420, 1230, 1120 |
| 119 | 1.33(3H, t), 1.67(3H, s), 1.75(3H, s), 4.07(2H, q), 6.75 (1H, d), 6.90(1H, d), 6.92(1H, d), 7.26(1H, dd), 7.40(1H, dd), 7.96(1H, d) | 1640, 1430 |
| 120 | 1.28(3H, t), 1.71(6H, s), 4.04(2H, q), 6.76(1H, d), 6.97 (1H, d), 7.32-7.34(2H, m), 7.40(1H, dd), 8.31(1H, dd) | |
| 121 | 1.30(3H, t), 1.70(6H, s), 4.04(2H, q), 6.99(1H, s), 7.08 (1H, s), 7.32-7.35(2H, m), 8.30(1H, m) | |
| 122 | 1.75(6H, s), 3.81(3H, s), 6.91(1H, d), 7.16(1H, d), 7.32-7.44 (2H, m), 7.57(1H, dd), 8.34(1H, dd) | 2220, 1640, 1280, 1120 |
| 123 | 1.71(6H, s), 3.81(3H, s), 7.01(1H, s), 7.06(1H, s), 7.30-7.43 (2H, m), 8.33(1H, dd) | |
| 124 | 1.23&1.31(3H, each t), 1.70, 1.78, 1.84&1.85(6H, each s), 4.08(2H, q), 6.88-7.14(3H, m), 7.23-7.35(1H, m), 7.49&7.55(1H, each m), 7.97&8.02(1H, each d) | 1630, 1420, 1280, 1120 |
| 125 | 1.73, 1.77, 1.84&1.86(6H, each s), 3.84&3.86(3H, each s), 6.88-7.12(3H, m), 7.29-7.36(1H, m), 7.51&7.57(1H, each dd), 7.99&8.03(1H, dd) | 2220, 1630, 1420, 1240, 1090 |
| 126 | 1, 70, 1.73, 1.81&1.83(6H, each s), 3.84&3.85(3H, each s), 6.89-7.16(3H, m), 7.26-7.38(1H, m), 7.97-8.02(1H, m) | 1620, 1600, 1420, 1230, 1090 |
| 127 | 1.71&1.74(3H, each s), 1.83(3H, s), 2.18&2.27(3H, each s), 6.75-6.80(1H, m), 6.90-6.96(1H, m), 7.17-7.46(3H, m), 8.14-8.23(1H, m) | 3450, 1620, 1595, 1470, 1420, 1410, 1370, 1270, 1240 |
| 128 | 1.74, 1.77, 1.86&1.87(6H, each s), 2.19&2.29(3H, each s), 6.91-6.96(1H, m), 7.10-7.39(3H, m), 7.51-7.62(1H, m), 8.16-8.24(1H, m) | 2220, 1640, 1480, 1450, 1430, 1250 |
| 129 | 1.70, 1.73, 1.80&1.83(6H, each s), 3.84(3H, s), 6.72-6.79 (1H, m), 6.88-6.94(2H, m), 7.24-7.44(3H, m), 7.98& 8.03(1H, each dd) | 3440, 1560, 1500, 1480, 1420, 1380, 1270, 1250, 1240, 1090 |
| 130 | 1.83(6H, s), 6.78(1H, d), 6.95(1H, d), 7.30-7.43(3H, m), 8.22-8.29(1H, m) | 1620, 1590, 1510, 1470, 1410, 1270, 1245 |
| 131 | 1.84&1.85(6H, each s), 6.61-7.05(2H, m), 7.20-7.65(3H, m), 8.40(1H, dd) | |
| 132 | 1.78(6H, s), 6.90-6.98(1H, m), 7.12(1H, d), 7.49-7.68(3H, m), 8.39-8.45(1H, m) | |
| 133 | −0.04&−0.02(9H, each s), 0.84-0.93(2H, m), 1.69, 1.73, 1.80&1.83(6H, each s), 3.58-3.68(2H, m), 5.11-5.27(2H, m), 6.72-6.93(2H, m), 7.15-7.43(3H, m), 7.98-8.06(1H, m) | EI-MS; m/z 480(M + 1), 478(M − 1) |
| 134 | 1.71(6H, s), 3.80(3H, s), 6.76(1H, d), 6.94(1H, d), 7.34-7.44 (3H, m), 8.33(1H, dd) | EI-MS; m/z 347(M$^+$) 348(M + 1) |
| 135 | 1.72(6H, s), 6.78(1H, d), 6.91(1H, d), 7.29-7.47(2H, m), 7.85(1H, dd), 8.63(1H, dd) | EI-MS; m/z 352(M$^+$) |
| 136 | 1.70(6H, s), 2.33(3H, s), 6.76(1H, d), 7.00(1H, d), 7.24-7.45 (1H, m), 7.58-7.66(1H, m), 8.51-8.55(1H, m) | EI-MS; m/z 330(M − 1), 331(M$^+$), 332(M + 1) |
| 137 | −0.03(9H, s), 0.86-0.94(2H, m), 1.71(6H, s), 3.60-3.69 (2H, m), 5.18(2H, s), 6.76(1H, d), 6.96(1H, d), 7.31-7.43 (2H, m), 7.59(1H, dd), 8.38(1H, dd) | EI-MS; m/z 464(M + 1), 462(M − 1) |
| 138 | 1.74(6H, s), 3.79(3H, s), 6.93(1H, d), 7.08(1H, d), 7.32-7.43 (2H, m), 7.55(1H, dd), 8.34(1H, dd) | |
| 139 | 1.24(3H, t), 1.74(6H, s), 4.03(2H, q), 6.94(1H, d), 7.12 (1H, d), 7.30-7.41(2H, m), 7.56(1H, dd), 8.33(1H, dd) | |
| 140 | 1.74(6H, s), 2.36(3H, s), 6.92(1H, d), 7.25-7.36(2H, m), 7.58(1H, dd), 7.63-7.69(1H, m), 8.54(1H, dd) | EI-MS; m/z 277(M$^+$), 276(M − 1) |
| 141 | 1.74(6H, s), 6.78-6.88(1H, m), 7.29-7.59(3H, m), 8.16 (1H, dd), 8.88(1H, dd) | 2230, 1625, 1440, 1330, 1275, 1260, 1160 |
| 142 | 1.78(6H, s), 6.96(1H, d), 7.55-7.67(2H, m), 7.79(1H, d), 8.19(1H, dd), 8.89(1H, dd) | 2230, 1630, 1490, 1440, 1340, 1280, 1125 |
| 143 | 1.63, 1.67, 2.00&2.05(6H, each s), 6.75-7.00(2H, m), 7.05-7.47(3H, m), 7.91&7.99(1H, each dd) | 1640, 1570, 1485, 1430, 1270, 1250, 1200, 1035 |
| 144 | 1.38(18H, S), 1.73(6H, S), 6.91(1H, d), 7.34-7.47(4H, m), 7.79(1H, dd), 8.25(1H, m) | 1800, 1710, 1280, 1100, EI-MS; m/z 497(M$^+$) |
| 145 | 1.70(6H, S), 4.51(2H, S), 6.85(1H, d), 6.92(1H, d), 7.30-7.48 (4H, m), 8.24(1H, m) | 3600-3200, 1640, 1430, 1240 |
| 146 | 1.74(6H, S), 6.98(1H, d), 7.38-7.50(4H, m), 7.88(1H, dd), 8.29(1H, m), 9.77(1H, S) | 1690, 1630, 1110 |

*(DMSO-d$_6$ + CDCl$_3$)

The following Experiments illustrate the pharmacological activities of the 1,3-benzoxazine derivatives of the general formula (I).

Vasorelaxation Activity in Rat Aorta Sample

Effect on Relaxation Caused by Tetraethylammonium Chloride (TEA) and Barium Chloride (Ba)

Method: Male Wister rats (10 to 13 weeks old) were used for the experiment. After dehematization, the aorta was excised and a ring sample (5 mm) was prepared. The sample was suspended in a bath filled with oxygenated (95% $O_2$-5% $CO_2$) Krebs solution (36° C.). The ring sample was fixed at one end and the other end was connected to a transducer (Nippon Koden, Japan) for recording tension and the tension was measured. After a stabilization period of 1 hour, TEA (30 to 45 mM) and Ba (0.3 mM) were added to the bath to cause vasoconstriction. After the constriction has reached a steady state (after about 15 minutes), a test compound was added to the bath and its relaxation activity was measured.

Result: The results are shown in Table 3 in terms of the inhibitory ratio of the test compound.

EXPERIMENT 2

Vasorelaxation Activity in Rat Aorta Sample

Effect on Relaxation Caused by Potassium Chloride (KCl)

Method: According to the same manner as that described in Experiment 1, this experiment was carried out except that KCl (80 mM) was used instead of TEA and Ba.

Result: The results are shown in Table 4 in terms of the inhibitory ratio of the test compound.

EXPERIMENT 3

Hypotensive Activity in Rats

Method: A spontaneously hypertensive rat (male, 20 to 23 weeks old) was operated in advance for retaining a cannula for blood pressure measurement in the left femoral artery. The experiment was carried out for the rat when waking on the next day after the operation. The cannula was connected with a transducer (Specrtramed) upon the experiment and the blood pressure was measured (Nippon Koden, Japan). A test compound was suspended in gum arabic and the suspension was administered orally.

Result: Mean ratio of maximum decrease in the blood pressure (mmHg) is shown in Table 5.

TABLE 3

| Comp. No. | constriction inhibitory ratio (%) | | |
|---|---|---|---|
| | 1 μM | 3 μM | 10 μM |
| 20 | | 35 | 81 |
| 23 | 19 | 82 | 100 |
| 24 | | 76 | 94 |
| 29 | 74 | | |
| 47 | 72 | 100 | |
| 49 | 28 | 77 | 86 |
| 53 | | | 89 |
| 65 | | 48 | 74 |
| 69 | | 45 | 81 |
| 75 | 38 | 91 | 100 |
| 77 | | 45 | 98 |
| 79 | 24 | 57 | 65 |
| 89 | 59 | 67 | 71 |
| 93 | 52 | 71 | |

TABLE 4

| Comp. No. | constriction inhibitory ratio (%) | | |
|---|---|---|---|
| | 1 μM | 3 μM | 10 μM |
| 20 | | −4 | −2 |
| 23 | −1 | 1 | 4 |
| 24 | | | −11 |
| 29 | −8 | | |
| 47 | −1 | 2 | |
| 49 | −7 | −6 | −3 |
| 53 | | | −4 |
| 65 | | −2 | 0 |
| 69 | | −1 | 2 |
| 75 | −2 | 1 | 2 |
| 77 | | 3 | 10 |
| 79 | −5 | −1 | 3 |
| 89 | −11 | −8 | −3 |
| 98 | −4 | −6 | |

TABLE 5

| Comp. No. | dose (mg/kg) | maximum effect (%) |
|---|---|---|
| 20 | 1.0 | 39 |
| 23 | 1.0 | 32 |
| 24 | 1.0 | 38 |
| 29 | 1.0 | 61 |
| 38 | 1.0 | 58 |
| 56 | 1.0 | 22 |
| 69 | 1.0 | 44 |
| 75 | 1.0 | 54 |
| 77 | 1.0 | 25 |
| 79 | 1.0 | 36 |
| 89 | 1.0 | 33 |
| 91 | 1.0 | 39 |
| 93 | 1.0 | 22 |
| 95 | 1.0 | 55 |
| 117 | 1.0 | 54 |
| 118 | 1.0 | 43 |
| 119 | 1.0 | 61 |
| 124 | 1.0 | 48 |
| 125 | 1.0 | 23 |
| 126 | 1.0 | 49 |
| 129 | 1.0 | 55 |
| 143 | 1.0 | 54 |

As shown in Tables 3 to 5, the 1,3-benzoxazine derivatives of the present invention show excellent vasorelaxation activity based on potassium channel opening action and excellent hypotensive activity.

What is claimed is:

1. A compound of the formula (Ia):

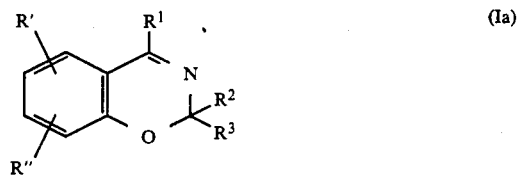

(Ia)

wherein R' and R" are independently (1) a hydrogen atom, (2) a hydroxyl group, (3) a halogen atom, (4) a nitro group, (5) a cyano group, (6) a $C_{1-6}$ alkyl group, (7) a $C_{1-6}$ alkoxy group, (8) a $C_{2-6}$ alkenyl group, (9) an ethynyl group, (10) a phenyl, naphthyl, or anthryl group, (11) furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl isoquinolyl or quinazolinyl, (12) an amino group, (13) a formyl group, (14) a substituted carbonyl group, (15) a carboxyl group, (16) a substituted carbonyloxy group, (17) a substituted thiocarbonyl group, (18) a substituted thiocarbonyloxy group, '19) an iminoalkyl group, (20) a mercapto group, (21) a sulfinyl group or (22) a sulfonyl group, or R' and R" are linked together to form —CH=CH—CH=CH—, which is optionally substituted with 1 to 3 substituents selected from the group consisting of $C_{1-4}$ alkyl, $C_{1-4}$ alkoxy, nitro, halogen, $CF_3$, $C_{1-4}$ alkoxycarbonyl and cyano, =N—O—N=, —(CH$_2$)$_a$— (wherein a is 3 or 4), —(CH$_2$)$_b$—CO—, —(CH$_2$)$_b$—C(=NOH)— or —(CH$_2$)$_b$13 C(=N—O—alkyl)- (wherein b is 2 or 3), the groups (6), (7), (8), (10) and (11) optionally being substituted with (a) $C_{1-4}$ alkyl, (b) $C_{1-4}$ alkoxy, (c) a phenyl, naphthyl, or anthryl group, which may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (d) $C_{6-14}$ aryl-$C_{1-4}$ alkyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (e) hydroxyl, (f) nitro, (g) halogen or (h) cyano, the group (9) optionally being substituted with (a) $C_{1-4}$ alkyl, (b) $C_{1-4}$ alkoxy, (c) a phenyl, naphthyl, or anthryl group, which may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (d) $C_{6-14}$ aryl-$C_{1-4}$alkyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (e) hydroxyl, (f) nitro, (g) halogen, (h) cyano or (i) trimethylsilyl, the group (12) optionally being substituted with (a) $C_{1-4}$ alkyl, (b) $C_{1-4}$ alkoxy, (c) halo $C_{1-4}$ alkyl, (d) formyl, (e) thioformyl, (f) hydroxyl, (g) carbamoyl, (h) a phenyl, naphthyl, or anthryl group, which may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (i) $C_{6-14}$ aryl-$C_{1-4}$ alkyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (j) $C_{1-4}$ alkylcarbonyl, (k) $C_{6-14}$ arylcarbonyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (l) $C_{6-14}$ aryl-$C_{1-4}$ alkylcarbonyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (m) $C_{1-4}$ alkyloxycarbonyl, (n) $C_{6-14}$ aryloxycarbonyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (o) $C_{6-14}$ aryl-$C_{1-4}$ alkyloxycarbonyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (p) furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl, isoquinolyl or quinazolinyl, which may be substituted with $C_{1-4}$ alkyl, $C_{1-4}$ alkoxy, hydroxyl, nitro, halogen, or cyano, (q) $C_{1-4}$ alkylsulfinyl, (r) $C_{1-4}$ alkoxysulfinyl, (s) $C_{6-14}$ arylsulfinyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (t) $C_{1-4}$ alkylsulfonyl, (u) $C_{1-4}$ alkoxysulfonyl or (v) $C_{6-14}$ arylsulfonyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, the groups (14), (16), (17) and (18) being substituted with (a) $C_{1-4}$ alkyl, (b) amino, (c) $C_{1-4}$ alkylamino, (d) $C_{1-4}$ alkyloxycarbonylamino, (e) $C_{6-14}$ arylamino where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (f) $C_{6-14}$ aryl-$C_{1-4}$ alkylamino where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (g) heteroarylamino wherein the heteroaryl is furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl, isoquinolyl or quinazolinyl, which may be substituted with $C_{1-4}$ alkyl, $C_{1-4}$ alkoxy, hydroxyl, nitro, halogen, or cyano, (h) heteroaryl-$C_{1-4}$ alkylamino wherein the heteroaryl is furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl, isoquinolyl or quinazolinyl, which may be substituted with $C_{1-4}$ alkyl, $C_{1-4}$ alkoxy, hydroxyl, nitro, halogen, or cyano, (i) a phenyl, naphthyl, or anthryl group, which may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (j) $C_{6-14}$ aryl-$C_{1-4}$ alkyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (k) heteroaryl-$C_{1-4}$ alkyl wherein the heteroaryl is furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl, isoquinolyl or quinazolinyl, which may be substituted with $C_{1-4}$ alkyl, $C_{1-4}$ alkoxy, hydroxyl, nitro, halogen, or cyano, or (l) furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl, isoquinolyl or quinazolinyl, which may be substituted with $C_{1-4}$ alkyl, $C_{1-4}$ alkoxy, hydroxyl, nitro, halogen, or cyano, the group (15) optionally being substituted with $C_{1-4}$ alkyl or $C_{6-14}$ aryl-$C_{1-4}$ alkyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, the group (19) optionally being substituted with (a) hydroxyl, (b) amino, (c) $C_{1-4}$ alkyl, (d) $C_{1-4}$ alkoxy, (e) a phenyl, naphthyl, or anthryl group, which may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (f) $C_{6-14}$ aryl-$C_{1-4}$ alkyloxy where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio or (g) heteroarylalkoxy where the heteroaryl is furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl, isoquinolyl or quinazolinyl, which may be substituted with $C_{1-4}$ alkyl, $C_{1-4}$ alkoxy, hydroxyl, nitro, halogen, or cyano, the group (20) optionally being substituted with (a) $C_{1-4}$ alkyl, (b) a phenyl, naphthyl, or anthryl group, which may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (c) furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl, isoquinolyl or quinazolinyl, which may be substituted with $C_{1-4}$ alkyl, $C_{1-4}$ alkoxy, hydroxyl, nitro, halogen, or cyano, (d) $C_{6-14}$ aryl-$C_{1-4}$ alkyl where the aryl moiety is a phenyl, naphthyl, or anthryl group, and may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio or (e) halo $C_{1-4}$ alkyl, the groups (21) and (22) optionally being substituted with (a) $C_{1-4}$ alkyl, (b) $C_{1-4}$ alkoxy, (c) a phenyl, naphthyl, or anthryl group, which may be substituted with $C_{1-4}$ alkyl, $C_{1-4}$ alkoxy, hydroxyl, nitro, halogen, halo $C_{1-4}$ alkyl, cyano, halo $C_{1-4}$ alkoxy, mercapto or halo $C_{1-4}$ alkylthio, (d) furyl, thienyl, pyrrolyl, oxazolyl, thiazolyl, imidazolyl, oxadiazolyl, thiadiazolyl, pyridyl, pyridazinyl, pyrimidinyl, pyrazinyl, triazinyl, benzofuranyl, benzothienyl, indolyl, indazolyl, quinolyl, isoquinolyl or quinazolinyl, which may be substituted with $C_{1-4}$ alkyl, $C_{1-4}$ alkoxy, hydroxyl, nitro, halogen, or cyano, (e) $C_{6-14}$ aryl-$C_{1-4}$ alkyl where the aryl moiety is a phenyl, naphthyl, or anthryl group, and may be substituted with $C_{1-4}$ alkyl, hydroxyl, nitro, halogen, halo $C_{1-4}$ alkyl, cyano, halo $C_{1-4}$ alkoxy, mercapto or halo $C_{1-4}$ alkylthio or (f) amino;

$R^1$ is phenyl, tolyl, methoxyphenyl, dimethoxyphenyl, trimethoxyphenyl, hydroxyphenyl, halogenophenyl, nitrophenyl, $CF_3$-phenyl, $CF_3O$-phenyl, cyanophenyl, carboxyphenyl, methoxycarbonylphenyl, ethoxycarbonylphenyl, aminophenyl, acetamidophenyl, methylthiophenyl, methylsulfinylphenyl, methanesulfonylphenyl, benzenesulfonylphenyl, toluenesulfonylphenyl, hydroxyethoxyphenyl, hydroxypropoxyphenyl, hydroxyethylaminocarbonylphenyl, nitroxyethoxyphenyl, nitroxypropoxyphenyl, nitroxyethylaminocarbonylphenyl, [3-(t-butyl)-2-cyano (or nitro) guanidino]phenyl, ]3-(1,2,2-trimethylpropyl)-2-cyano (or nitro) guanidino]phenyl, 2-pyridyl, 3-pyridyl, 4-pyridyl, 1-methylpyridinium-2-yl, 1-methylpyridinium-3-yl, 1-methylpyridinium-4-yl, pyridin-N-oxide-2-yl, pyridin-N-oxide-3-yl, pyridin-N-oxide-4-yl, (di)methylpyridin 2,3- or 4-yl, (di)methylpyridin-N-oxide-2,3 or 4-yl, hydroxypyridin-2,3 or 4-yl, hydroxypyridin-N-oxide-2,3 or 4-yl, methoxypyridin-2,3 or 4-yl, methoxypyridin-N-oxide-2,3 or 4-yl, ethoxypyridin-2,3 or 4-yl, ethoxypyridin-N-oxide-2,3- or 4-yl, halogenopyridin-2,3 or 4-yl, halogenopyridin-N-oxide-2,3 or 4-yl, nitropyridin-2,3 or 4-yl, nitropyridin-N-oxide-2,3 or 4-yl, aminopyridin-2,3 or 4-yl, aminopyridin-N-oxide-2,3 or 4-yl, trifluoromethylpyridin-2,3 or 4-yl, trifluoromethylpyridin-N-oxide-2,3 or 4-yl, nitroxyethoxypyridin-2,3 or 4-yl, nitroxyethoxypyridin-N-oxide-2,3 or 4-yl, carboxypyridin-2,3 or 4-yl, carboxypyridin-N-oxide-2,3 or 4-yl, methoxycarbonylpyridin-2,3 or 4-yl, methoxycarbonylpyridin-N-oxide-2,3 or 4-yl, ethoxycarbonylpyridin-2,3 or 4-yl, ethoxycarbonylpyridin-N-oxide-2,3 or 4-yl, carbamoylpyridin-2,3 or 4-yl, carbamoylpyridin-N-oxide-2,3 or 4-yl, cyanopyridin-2,3 or 4-yl, cyanopyridin-N-oxide-2,3 or 4-yl, nitroxyethylaminocarbonylpyridin-2,3 or 4-yl, nitroxyethylaminocarbonylpyridin-N-oxide-2,3 or 4-yl, [3-methyl-2-cyano (or nitro) guanidino]pyridin-2,3 or 4-yl, [3-methyl-2-cyano (or nitro) guanidino]pyridin-N-oxide-2,3 or 4-yl, [3-(t-butyl)-2-cyano (or nitro) guanidino]pyridin-2,3 or 4-yl, [3-(t-butyl)-2-cyano (or nitro) guanidino]pyridin-N-oxide-2,3 or 4-yl, [3-(1,2,2-trimethylpropyl)-2-cyano (or nitro) guanidino]pyridin-2,3 or 4-yl, [3-(1,2,2-trimethylpropyl)-2-cyano (or nitro) guanidino]pyridin-N-oxide-2,3 or 4-yl, acetamidopyridin-2,3 or 4-yl, acetamidopyridin-N-oxide-2,3 or 4-yl, methanesulfonylpyridin-2,3 or 4-yl, methanesulfonylpyridin-N-oxide-2,3 or 4-yl, toluenesulfonylpyridin-2,3 or 4-yl, toluenesulfonylpyridin-N-oxide-2,3 or 4-yl, halogenonitropyridin-2,3 or 4-yl, halogeno-nitropyridin-N-oxide-2,3 or 4-yl, methyl-nitropyridin-2,3 or 4-yl, methylnitropyridin-N-oxide-2,3 or 4-yl, amino-nitropyridin-2,3 or 4-yl, amino-nitropyridin-N-oxide-2,3 or 4-yl, trifluoromethyl-halogenopyridin-2,3 or 4-yl, trifluoromethyl-halogenopyridin-N-oxide-2,3 or 4-yl, cyano-nitropyridin-2,3 or 4-yl, cyano-nitropyridin-N-oxide-2,3 or 4-yl, methyl-nitroxyethylaminocarbonylpyridin-2,3 or 4-yl, methyl-nitroxyethylaminocarbonylpyridin-N-oxide-2,3 or 4-yl, 3-pyridazinyl, 4-pyridazinyl, 6-methylpyridazin-3-yl, 6-methoxypyridazin-3-yl, 6-chlorophyidazin-3-yl, pyridazin-N-oxide-3 or 4-yl, 6-methylpyridazin-N-oxide-3-yl, 6-methoxypyridazin-N-oxide-3-yl, 6-chloropyridazin-N-oxide-3-yl, 4-pyrimidinyl, 5-pyrimidinyl, 6-methylpyrimidin-4-yl, pyrimidin-N-oxide-4 or 5-yl, 6-methylpyrimidin-N-oxide-4-yl, 2-pyrazinyl, pyrazin-N-oxide-2 or 3-yl, 2-quinolinyl, 3-quinolinyl, 4-quinolinyl, nitroquinolin-2-yl, chloroquinolin-2-yl, methylquinolin-2-yl, methoxyquinolin-2-yl, quinolin-N-oxide-2,3 or 4-yl, nitroquinolin-N-oxide-2-yl, chloroquinolin-N-oxide-2-yl, methylquinolin-N-oxide-2-yl, methoxyquinolin-N-oxide-2-yl, isoquinolin-1,3 or 4-yl, isoquinolin-N-oxide-1,3 or 4-yl, 2- or 3-indolyl, N-acetylindol-2 or 3-yl, N-benzylindol-2 or 3-yl, N-methylsulfonylindol-2 or 3-yl, N-benzenesulfonylindol-2 or 3-yl, N-tosylendol-2 or 3-yl, 2 or 3-pyrrolyl, N-acetylpyrrol-2 or 3-yl, N-benzylpyrrol-2 or 3-yl, N-methylsulfonylpyrrol-2 or 3-yl, N-benzenesulfonylpyrrol-2 or 3-yl, N-tosylpyrrol-2 or 3-yl, groups of the formulas:

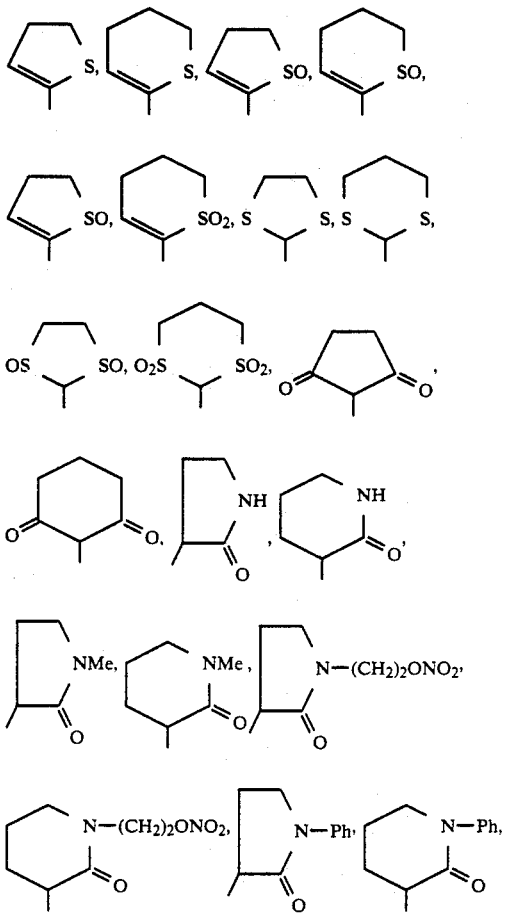

2,2-dimethyl-1,3-dioxan-4,6-dione-5-yl, (CH$_3$S)$_2$CH—, (PhS)$_2$CH—, (CH$_3$SO)$_2$CH—, (PhSO)$_2$CH—, (CH$_3$SO$_2$)$_2$CH—, (PhSO$_2$)$_2$CH—, Ac$_2$CH—, or (PhCO)$_2$CH—, R$^2$ and R$^3$ are a C$_{1-6}$ alkyl group, or R$^2$ and R$^3$ are linked together to form a C$_{3-6}$ alkylene group; or a pharmaceutically acceptable salt thereof.

2. A compound according to claim 1, wherein R' and R" are methyl, ethyl, acetyl, propionyl, benzoyl (optionally substituted with methyl, methoxy, halogen, nitro, CF$_3$ or cyano), methoxy, ethoxy, methoxycarbonyl, ethoxycarbonyl, acetoxy, propioxy, propoxycarbonyl, butyloxycarbonyl, isobutyloxycarbonyl, 1-hydroxyethyl, 1-hydroxybenzyl, methylsulfinyl, ethylsulfinyl, benzenesulfinyl (optionally substituted with methyl, methoxy, halogen, nitro, CF$_3$ or cyano), methylsulfonyl, ethylsulfonyl, benzenesulfonyl (optionally substituted with methyl, ethoxy, halogen, nitro, CF$_3$ or cyano), methoxysulfinyl, ethoxysulfinyl, methoxysulfonyl, ethoxysulfonyl, acetamido, propionamido, benzamido (optionally substituted with methyl, methoxy, halogen, nitro, CF$_3$ or cyano), methoxycarbonylamido, ethoxycarbonylamido, thioacetyl, thiopropionyl, thiobenzoyl (optionally substituted with methyl, methoxy, halogen, nitro, CF$_3$ or cyano), methoxythiocarbonyl, ethoxythiocarbonyl, thionoacetoxy, thionopropionoxy, 1-mercaptoethyl, 1-mercaptobenzyl, methylsulfinylamino, ethylsulfinylamino, benzenesulfinylamino (optionally substituted with methyl, methoxy, halogen, nitro, CF$_3$ or cyano), methylsulfonylamino, ethylsulfonylamino, benzenesulfonylamino (optionally substituted with methyl, methoxy, halogen, nitro, CF$_3$ or cyano), methoxylsulfinylamino, ethoxylsulfinylamino, methoxysulfonylamino, ethoxysulfonylamino, 1-propenyl, styryl (optionally substituted with methyl, methoxy, halogen, nitro, CF$_3$ or cyano), methoxyiminomethyl, ethoxyiminomethyl, 1-(hydroxyimino)ethyl, 1-(hydroxyimino)propyl, 1-hydrazinoethyl, 1-hydrazinopropyl, 1-propynyl, CF$_3$, CF$_3$CF$_2$, CF$_3$O, HCF$_2$O, CF$_2$=CF, nitro, cyano, halogen, amino, formyl, formamido, hydroxyiminomethyl, CO$_2$H, CONH$_2$, SH, CF$_3$S, thioformamido, CSNH$_2$, SO$_2$NH$_2$, 2-oxopropyl, 2-oxobutyl, 3-oxobutyl, 3-oxopentyl, nitromethyl, 1-nitroethyl, 2-nitroethyl, vinyl, nitrovinyl, cyanovinyl, trifluorovinyl, ethynyl or (CH$_3$)$_3$SiC≡C.

3. A compound according to claim 1, wherein R' or R" is furyl, thienyl, pyrrolyl, oxazolyl, thiazolyl, imidazolyl, oxadiazolyl, thiadiazolyl, pyridyl, pyridazinyl, pyrimidinyl, pyrazinyl or triazinyl, which is optionally substituted with methyl, methoxy, halogen, CF$_3$, nitro or cyano.

4. A compound according to claim 1, wherein R' and R" are linked together to form —CH=CH—CH=CH— (optionally substituted with methyl, methoxy, halogen, nitro, CF$_3$ or cyano), =N—O—N=, —(CH$_2$)$_3$—, —(CH$_2$)$_4$—, —(CH$_2$)$_2$CO—, —(CH$_2$)$_3$CO—, —(CH$_2$)$_2$C(=NOH)—, —(CH$_2$)$_2$C(=NOCH$_3$)—, —(CH$_2$)$_3$C(=NOH)— or (CH$_2$)$_3$C(=NOCH$_3$)—.

5. A compound according to claim 1, wherein R$^1$ is 2-pyridyl optionally substituted with hydroxyl, C$_{1-6}$ alkoxy, C$_{1-6}$ alkyl or halogen, pyridine-N-oxide-2-yl optionally substituted with hydroxyl, C$_{1-6}$ alkoxy, C$_{1-6}$ alkyl or halogen, 2-quinolyl, quinoline-N-oxide-2-yl or 1-methyl-2-oxo-3-pyrrolidinyl.

6. A compound according to claim 1, wherein R$^1$ is 3-methyl-2-(cyano or nitro)-guanidino, 3,3-dimethyl-2-(cyano or nitro)-guanidino, 3-(t-butyl)-2-(cyano or nitro)-guanidino, 3-(1,2,2-trimethylpropyl)-2-(cyano or nitro)-guanidino, 3-isopropyl-2-(cyano or nitro)-guanidino, 3-cyclopropyl-2-(cyano or nitro)-guanidino, 3,3-tetramethylene-2-(cyano or nitro)-guanidino, 3,3-pentamethylene-2-(cyano or nitro)-guanidino, (1-methylamino-2-nitroethenyl)amino, (1-isopropylamino-2-nitroethenyl)amino, 2-methyl-3-(cyano or nitro)-1-isothioureido, (1-methylthio-2-nitroethenyl)amino, 2-methyl-3-(cyano or nitro)-1-isoureido, 2-ethyl-3-(cyano or nitro)-1-isoureido, (1-methoxy-2-nitroethenyl)amino, (1-ethoxy-2-nitroethenyl)amino, 2-cyanoimino-imidazolidin-1-yl, 2-nitroimino-imidazolidin-1-yl, 2-(cyanoimino or nitroimino)-hexahydropyrimidin-1-yl, 2-nitroethenylimidazolidin-1-yl, 2-nitroethenyl-hexahydropyrimidin-1-yl, 2-(cyanoimino or nitroimino)-thiazolidin-3-yl, 2-nitroethenyl-thiazolidin-3-yl, 2-(cyanoimino or nitroimino)-oxazolidin-3-yl, 2-nitroethenyl-oxazolidin-3-yl, or 2-(cyano or nitro)-creatinin-3-yl.

7. A compound according to claim 1, wherein R$^2$ and R$^3$ are independently methyl, ethyl or propyl.

8. A compound according to claim 1, wherein $R^2$ and $R^3$ are linked together to form cyclopropyl, cyclopentyl or cyclohexyl.

9. A compound according to claim 1 which is:

2,2-dimethyl-4-(2-pyridyl)-2H-1,3-benzoxazine,
2-(6-bromo-2,2-dimethyl-2H-1,3-benzoxazin-4-yl)pyridine N-oxide,
2-(6-cyano-2,2-dimethyl-2H-1,3-benzoxazin-4-yl)pyridine N-oxide,
2-(2,2-dimethyl-6-nitro-2H-1,3-benzoxazin-4-yl)pyridine N-oxide,
2-(6-acetyl-2,2-dimethyl-2H-1,3-benzoxazin-4-yl)pyridine N-oxide,
2-(6-cyano-2,2-dimethyl-7-nitro-2H-1,3-benzoxazin-4-yl)pyridine N-oxide,
2-(6-methoxycarbonyl-2,2-dimethyl-2H-1,3-benzoxazin-4-yl)pyridine N-oxide,
2-(6-ethynyl-2,2-dimethyl-2H-1,3-benzoxazin-4-yl)pyridine N-oxide,
2-(6-chloro-2,2-dimethyl-2H-1,3-benzoxazin-4-yl)pyridine N-oxide,
2-(6-bromo-2,2,7-trimethyl-2H-1,3-benzoxazin-4-yl)pyridine N-oxide,
2-(2,2,7-trimethyl-6-nitro-2H-1,3-benzoxazin-4-yl)pyridine N-oxide,
2-(6-cyano-2,2,7-trimethyl-2H-1,3-benzoxazin-4-yl)pyridine N-oxide,
2-(6-bromo-7-methoxy-2,2-dimethyl-2H-1,3-benzoxazin-4-yl)pypyridine N-oxide,
2-(7-methoxy-2,2-dimethyl-6-nitro-2H-1,3-benzoxazin-4-yl)pyridine N-oxide,
2-(6-cyano-7-methoxy-2,2-dimethyl-2H-1,3-benzoxazin-4-yl)pyridine N-oxide,
2-(6-bromo-7-fluoro-2,2-dimethyl-2H-1,3-benzoxazin-4-yl)pyridine N-oxide,
2-(6-cyano-7-fluoro-2,2-dimethyl-2H-1,3-benzoxazin-4-yl)pyridine N-oxide,
2-(7-fluoro-2,2-dimethyl-6-nitro-2H-1,3-benzoxazin-4-yl)pyridine N-oxide,
2-(6-trifluoromethyl-2,2-dimethyl-2H-1,3-benzoxazin-4-yl)pyridine N-oxide,
2-(6-trifluoromethoxy-2,2-dimethyl-2H-1,3-benzoxazin-4-yl)pyridine N-oxide,
2-(6-pentafluoroethyl-2,2-dimethyl-2H-1,3-benzoxazin-4-yl)pyridine N-oxide,
2-(6-trifluorovinyl-2,2-dimethyl-2H-1,3-benzoxazin-4-yl)pyridine N-oxide,
2-(6,7-dichloro-2,2-dimethyl-2H-1,3-benzoxazin-4-yl)pyridine N-oxide,
2-(6-bromo-7-chloro-2,2-dimethyl-2H-1,3-benzoxazin-4-yl)pyridine N-oxide,
2-(7-chloro-6-cyano-2,2-dimethyl-2H-1,3-benzoxazin-4-yl)pyridine N-oxide,
2-(6,7-dibromo-2,2-dimethyl-2H-1,3-benzoxazin-4-yl)pyridine N-oxide,
2-(2,2-dimethyl-2H-naphtho[2,3-e][1,3]oxazin-4-yl)pyridine N-oxide,
2-(6-cyano-2,2-dimethyl-2H-1,3-benzoxazin-4-yl)-3-ethoxypyridine N-oxide,
6-cyano-2,2-dimethyl-4-(1-methyl-2-oxo-3-pyrrolidinyl)-2H-1,3-benzoxazine,
2-(6-bromo-2,2-dimethyl-2H-1,3-benzoxazin-4-yl)quinoline N-oxide,
2-(6-cyano-2,2-dimethyl-2H-1,3-benzoxazin-4-yl)-3-methoxypyridine N-oxide,
2-(6-cyano-2,2-dimethyl-2H-1,3-benzoxazin-4-yl)-3-hydroxypyridine N-oxide,
2-(6-cyano-2,2-dimethyl-2H-1,3-benzoxazin-4-yl)-3-methylpyridine N-oxide,
3-chloro-2-(6-cyano-2,2-dimethyl-2H-1,3-benzoxazin-4-yl)pyridine N-oxide,
2-(6-bromo-2,2-dimethyl-2H-1,3-benzoxazin-4-yl)-3-methoxypyridine N-oxide,
2-(6-bromo-2,2-dimethyl-2H-1,3-benzoxazin-4-yl)-3-ethoxypyridine N-oxide,
2-(6-bromo-2,2-dimethyl-2H-1,3-benzoxazin-4-yl)-3-methylpyridine N-oxide,
2-(6-bromo-2,2-dimethyl-2H-1,3-benzoxazin-4-yl)-3-chloropyridine N-oxide,
2-(6-bromo-7-chloro-2,2-dimethyl-2H-1,3-benzoxazin-4-yl)-3-methoxypyridine N-oxide,
2-(6-bromo-7-chloro-2,2-dimethyl-2H-1,3-benzoxazin-4-yl)-3-ethoxypyridine N-oxide,
2-(6-bromo-7-chloro-2,2-dimethyl-2H-1,3-benzoxazin-4-yl)-3-methylpyridine N-oxide,
2-(6-bromo-7-chloro-2,2-dimethyl-2H-1,3-benzoxazin-4-yl)-3-chloropyridine N-oxide,
2-(6-trifluoromethyl-2,2-dimethyl-2H-1,3-benzoxazin-4-yl)-3-methoxypyridine N-oxide,
3-ethoxy-2-(6-trifluoromethyl-2,2-dimethyl-2H-1,3-benzoxazin-4-yl)pyridine N-oxide,
2-(6-trifluoromethyl-2,2-dimethyl-2H-1,3-benzoxazin-4-yl)-3-methylpyridine N-oxide, or
3-chloro-2-(6-trifluoromethyl-2,2-dimethyl-2H-1,3-benzoxazin-4-yl)pyridine N-oxide.

10. A compound which is 2-(6-bromo-7-chloro-2,2-dimethyl-2H-1,3-benzoxazin-4-yl)pyridine N-oxide.

11. A hypotensor which comprises an effective hypotensive amount of a compound of the formula (Ia) according to claim 1 or a pharmaceutically acceptable salt thereof.

12. A method for treating hypertension which comprises administering an effective amount of a compound of the formula (Ia) according to claim 1 or a pharmaceutically acceptable salt thereof optionally together with a pharmaceutically acceptable carrier, diluent or excipient to a patient suffering from hypertension.

* * * * *

UNITED STATES PATENT AND TRADEMARK OFFICE
CERTIFICATE OF CORRECTION

PATENT NO. : 5,270,308
DATED : December 14, 1993
INVENTOR(S) : Mitsuru SHIRAISHI et al.

It is certified that error appears in the above-identified patent and that said Letters Patent is hereby corrected as shown below:

Col. 52, line 16, Table 4 (last line), change Compound No. "98" to --93--.

Col. 52, line 63 (claim 1), between "quinolyl" and "isoquinolyl", insert --,--.

Col. 53, line 8 (claim 1), change "-(CH2)$_b$13C(=N-O-alkyl)-" to -- -(CH$_2$)$_b$-C(=N-O-alkyl)- --.

Signed and Sealed this

Nineteenth Day of July, 1994

Attest:

BRUCE LEHMAN

Attesting Officer

Commissioner of Patents and Trademarks